US011167154B2

(12) United States Patent
Alford et al.

(10) Patent No.: US 11,167,154 B2
(45) Date of Patent: Nov. 9, 2021

(54) ULTRASOUND DIAGNOSTIC AND THERAPY MANAGEMENT SYSTEM AND ASSOCIATED METHOD

(71) Applicant: Medtronic, Inc., Minneapolis, MN (US)

(72) Inventors: Jamu Alford, Ham Lake, MN (US); Steven M. Goetz, North Oaks, MN (US); Lothar Krinke, Eden Prairie, MN (US); Mark S. Lent, Brooklyn Park, MN (US); Erik R. Scott, Maple Grove, MN (US); Xuan K. Wei, Minnetonka, MN (US); John D. Welter, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/749,237

(22) Filed: Jan. 24, 2013

(65) Prior Publication Data
US 2014/0058292 A1 Feb. 27, 2014

Related U.S. Application Data

(60) Provisional application No. 61/692,022, filed on Aug. 22, 2012.

(51) Int. Cl.
*A61N 7/00* (2006.01)
*A61N 1/05* (2006.01)
(Continued)

(52) U.S. Cl.
CPC .............. *A61N 7/00* (2013.01); *A61B 5/0036* (2018.08); *A61B 8/0816* (2013.01);
(Continued)

(58) Field of Classification Search
CPC ........ A61N 7/00; A61N 1/36017; A61N 1/05; A61N 1/36071; A61N 1/0529;
(Continued)

(56) References Cited

U.S. PATENT DOCUMENTS 4,670,683 A * 6/1987 't Hoen ......................... 310/334
5,807,285 A   9/1998 Vaitekunas
(Continued)

FOREIGN PATENT DOCUMENTS

CN 102164542 A 8/2011
CN 102989089 A 3/2013
(Continued)

OTHER PUBLICATIONS

Haro et al. "Electro-sensitisation of mammalian cells and tissues to ultra-sound: a novel tumor treatment modality" 2005 Cancer Letters 222:49-55.*
(Continued)

*Primary Examiner* — Michael J Tsai
*Assistant Examiner* — Patrick M Mehl
(74) *Attorney, Agent, or Firm* — Shumaker & Sieffert, P.A.

(57) ABSTRACT

A system for use in managing a neuromodulation therapy includes an ultrasound transducer array controlled by a control unit to deliver ultrasound waveforms for causing modulation of neural tissue in a patient. The system acquires data indicating a response to the modulation, analyzes the acquired data to determine correlation data between a response to the modulation and an ultrasound control parameter, and reports the correlation data to enable identification of at least one therapy parameter to be used to deliver a neuromodulation therapy to the patient by a therapy delivery system.

44 Claims, 8 Drawing Sheets

(51) Int. Cl.
  *A61B 8/08* (2006.01)
  *A61B 5/00* (2006.01)
  *A61N 1/36* (2006.01)

(52) U.S. Cl.
  CPC ......... *A61N 1/0529* (2013.01); *A61N 1/0551* (2013.01); *A61B 5/40* (2013.01); *A61B 5/4848* (2013.01); *A61N 1/36062* (2017.08); *A61N 2007/0026* (2013.01); *A61N 2007/0043* (2013.01); *A61N 2007/0052* (2013.01); *A61N 2007/0095* (2013.01)

(58) Field of Classification Search
  CPC ........ A61N 1/372; A61N 1/0534; A61N 7/02; A61N 1/37205; A61N 1/36064; A61N 1/365; A61N 1/0568; A61N 1/36167; A61N 1/36514; A61N 1/36189; A61N 1/36528; A61N 1/04; A61N 1/3625; A61N 1/3702; A61N 1/0531; A61N 2007/0026; A61N 1/36521; A61N 1/0526; A61N 2007/0021
  USPC ......................................................... 600/439
  See application file for complete search history.

(56) References Cited

U.S. PATENT DOCUMENTS

| | | | |
|---|---|---|---|
| 6,267,734 B1* | 7/2001 | Ishibashi et al. | 601/2 |
| 6,484,059 B2 | 11/2002 | Gielen | |
| 6,675,038 B2* | 1/2004 | Cupples et al. | 600/424 |
| 6,926,660 B2 | 8/2005 | Miller | |
| 7,211,054 B1 | 5/2007 | Francis et al. | |
| 7,283,861 B2 | 10/2007 | Bystritsky | |
| 7,500,954 B2* | 3/2009 | Wilser et al. | 600/467 |
| 7,553,284 B2 | 6/2009 | Vaitekunas | |
| 7,699,768 B2 | 4/2010 | Kishawi | |
| 7,991,474 B2 | 8/2011 | Aldrich | |
| 8,032,224 B2 | 10/2011 | Miesel | |
| 8,086,296 B2 | 12/2011 | Bystritsky | |
| 8,197,409 B2 | 6/2012 | Foley | |
| 8,204,607 B2 | 6/2012 | Rooney | |
| 8,364,258 B2* | 1/2013 | Della Rocca et al. | 607/3 |
| 8,718,758 B2 | 5/2014 | Wagner et al. | |
| 2002/0095087 A1 | 7/2002 | Mourad et al. | |
| 2002/0198572 A1 | 12/2002 | Weiner | |
| 2004/0049134 A1 | 3/2004 | Tosaya et al. | |
| 2007/0066902 A1* | 3/2007 | Wilser et al. | 600/459 |
| 2007/0150025 A1* | 6/2007 | Dilorenzo | A61B 5/0476 607/45 |
| 2007/0239080 A1 | 10/2007 | Schaden et al. | |
| 2007/0255085 A1 | 11/2007 | Kishawi | |
| 2008/0269599 A1 | 10/2008 | Csavoy | |
| 2009/0005713 A1 | 1/2009 | Podrazhansky et al. | |
| 2009/0112133 A1* | 4/2009 | Deisseroth et al. | 601/3 |
| 2009/0112278 A1 | 4/2009 | Wingeier et al. | |
| 2009/0220136 A1* | 9/2009 | Bova et al. | 382/131 |
| 2009/0254134 A1 | 10/2009 | Nikolov | |
| 2010/0023089 A1* | 1/2010 | DiLorenzo | 607/45 |
| 2011/0024573 A1 | 2/2011 | Kirk et al. | |
| 2011/0027034 A1 | 2/2011 | Chamoun | |
| 2011/0029044 A1 | 2/2011 | Hyde | |
| 2011/0112394 A1 | 5/2011 | Mishelevich | |
| 2011/0130615 A1 | 6/2011 | Mishelevich | |
| 2011/0144573 A1 | 6/2011 | Rofougaran | |
| 2011/0152748 A1* | 6/2011 | Della Rocca et al. | 604/21 |
| 2011/0172527 A1* | 7/2011 | Gertner | 600/439 |
| 2011/0178441 A1 | 7/2011 | Tyler | |
| 2011/0178442 A1 | 7/2011 | Mishelevich | |
| 2011/0190668 A1 | 8/2011 | Mishelevich | |
| 2011/0196267 A1 | 8/2011 | Mishelevich | |
| 2011/0208094 A1 | 8/2011 | Mishelevich | |
| 2011/0213200 A1 | 9/2011 | Mishelevich | |
| 2011/0245734 A1* | 10/2011 | Wagner | A61N 1/36025 601/2 |
| 2011/0270138 A1 | 11/2011 | Mishelevich | |
| 2011/0270348 A1 | 11/2011 | Goetz | |
| 2012/0053391 A1 | 3/2012 | Mishelevich | |
| 2012/0083719 A1 | 4/2012 | Mishelevich | |
| 2012/0197163 A1 | 8/2012 | Mishelevich | |
| 2012/0220812 A1 | 8/2012 | Mishelevich | |
| 2012/0226091 A1 | 9/2012 | Mishelevich | |
| 2012/0226138 A1 | 9/2012 | DeSalles et al. | |
| 2012/0232433 A1 | 9/2012 | Mishelevich | |
| 2012/0245493 A1 | 9/2012 | Mishelevich | |
| 2012/0271171 A1 | 10/2012 | Gertner | |
| 2012/0283502 A1 | 11/2012 | Mishelevich | |
| 2012/0283604 A1 | 11/2012 | Mishelevich | |
| 2012/0289869 A1 | 11/2012 | Tyler | |
| 2012/0296241 A1 | 11/2012 | Mishelevich | |
| 2013/0184728 A1 | 7/2013 | Mishelevich | |
| 2013/0281890 A1 | 10/2013 | Mishelevich | |
| 2014/0058292 A1 | 2/2014 | Alford et al. | |
| 2014/0094720 A1 | 4/2014 | Tyler | |

FOREIGN PATENT DOCUMENTS

| | | |
|---|---|---|
| JP | 2002000613 A | 1/2002 |
| JP | 2005305013 A | 11/2005 |
| JP | 2008279274 A | 11/2008 |
| WO | 2011057028 A1 | 5/2011 |

OTHER PUBLICATIONS

Lai et al. "Noninvasive thermometry assisted by a dual function ultrasound transducer for mild hyperthermia" 2010 IEEE Trans. Ultrason Ferroelctr Freq Control 57:2671-2684.*
Haro et al. Electro-sensitisation of mammalian cells. 2005 Cancer Lett. 222:49-55.*
Mace et al. Functional ultrasound imaging of the brain. 2011 Nature Methods 8:662-666.*
Yoo et al. Focused ultrasound modulates region-specific brain activity. 2011 Neuroimage 56:1267-1275.*
Lu et al. 2009 Clin.Cancer Res. 15:876-886.*
Cardinal et al. 2008 Surgery 144:125-132.*
Bachtold et al., "Focused Ultrasound Modifications of Neural Circuit Activity in a Mammalian Brain," Ultrasound in Med. & Biol., vol. 24(4), May 1998, pp. 557-565.
Bystritsky et al., "A Review of Low-Intensity Focust Ultrasound Pulsation," Brain Stimulation, vol. 4, Jul. 2011, pp. 125-136.
Legon et al., "Pulsed Ultrasound Differentially Stimulates Somatosensory Circuits in Humans as Indicated by EEG and fMRI," PLOS One, vol. 7(12), Dec. 2012, 14 pp.
Mulgaonkar et al., "A Prototype Stimulator System for Noninvasive Low Intensity Focuses Ultrasound Delivery," Medicine Meets Virtual Reality 19, IOS Press, 2012, 8 pp. (Note: Applicant points out in accordance with MPEP 609.04(a) that the 2012 year of publication is sufficiently earlier than the effective U.S. filed and any foreign priority date of Jan. 24, 2013 so that the particular month of publication is not in issue.).
Spieles-Engemann et al., "Stimulation of the Rat Subthalamic Neclous is Neuroprotective Following Significant Nigral Dopamine Neuron Loss," Neurobiol. Dis., vol. 39(1), Jul. 2010, 24 pp.
Office Action from counterpart Japanese Application No. 2015-528451 dated Mar. 7, 2016, 13 pp.
International Search Report and Written Opinion, PCT/US2013/023090, dated May 22, 2013, 10 pps.
Examination Report from counterpart Australian Application No. 2013306411, dated Jun. 10, 2015, 2 pp.
Examination Report from counterpart Australian Patent Application No. 2013306411, dated Jan. 21, 2016, 3 pp.
First Office Action and Search Report, and translation thereof, from counterpart Chinese Application No. 201380042107.6, dated Mar. 30, 2017, 23 pp.
Examination Report from counterpart European Application No. 13703242.1, dated May 22, 2018, 5 pp.
Examination Report from counterpart European Application No. 13703242.1, dated Jan. 16, 2020, 5 pp.

(56) References Cited

OTHER PUBLICATIONS

Response to Examination Report from counterpart European Application No. 13703242.1, dated Jan. 16, 2020, filed May 29, 2020, 8 pp.

* cited by examiner

ULTRASOUND DIAGNOSTIC AND THERAPY MANAGEMENT SYSTEM AND ASSOCIATED METHOD

REFERENCE TO RELATED APPLICATIONS

This application claims the benefit of U.S. Patent Application No. 61/692,022, filed provisionally on Aug. 22, 2012, and entitled "ULTRASOUND DIAGNOSTIC AND THERAPY MANAGEMENT SYSTEM AND ASSOCIATED METHOD."

FIELD OF THE DISCLOSURE

The disclosure relates generally to a medical diagnostic and therapy management system, and, more specifically, a medical diagnostic and therapy management system that uses ultrasound waveforms focused on neural targets.

BACKGROUND

The number of evolving therapeutic treatments involving modulation of neural tissue using electrical stimulation is rising, such as Deep Brain Stimulation (DBS) for reducing tremor in Parkinson's disease, dystonia, and obsessive compulsive disorder, vagus nerve stimulation for treating epilepsy, hypertension and depression, and more. However, the number of patients seeking such treatments may be dramatically lower than the number of patients that may actually benefit due to the perceived risks and uncertainty on behalf of the patient of the potential benefit he/she could experience.

Neural disorders, which can be the underlying cause of mental illnesses, movement disorders, sensory disorders, visceral disorders, etc., can be difficult to diagnose. Even if diagnosed, the neural structure that is the source of the disorder may go unidentified precluding the full potential benefit of neuromodulation therapies.

A need remains for a diagnostic tool and associated method for diagnosing neural disorders, identifying patients that may benefit from neuromodulation, and planning or optimizing neuromodulation therapies including identifying therapeutic neural targets.

SUMMARY

A system for planning and delivering a neuromodulation therapy as disclosed herein uses external focused ultrasound to deliver neuromodulation to a patient. Data indicating a response to the neuromodulation is acquired and analyzed to identify a parameter for controlling a neuromodulation therapy by a therapy delivery system, which may use a different mode of neuromodulation than ultrasound.

In one embodiment, the system includes an external ultrasound transducer array comprising at least one ultrasound transducer and a control unit configured to control delivery of ultrasound waveforms for causing modulation of neural tissue in a patient, acquire data indicating a response to the modulation, analyze the acquired data to accumulate correlation data between a response to the modulation and an ultrasound control parameter, and report the correlation data to enable identification of at least one therapy parameter to be used to deliver a neuromodulation therapy to the patient by a therapy delivery system.

In some embodiments, acquiring data includes receiving reflections of ultrasound waveforms from the array. The ultrasound transducer array may be controlled to emit first ultrasound waveforms for causing neuromodulation and to emit second ultrasound waveforms and measure reflections received from the second waveforms. Measured reflections may be used to determine a functional response to neuromodulation or for imaging and identification of a target site. Neuromodulation waveforms may be focused at an identified target site by adjusting a selection of transducers of the array enabled to emit ultrasound waveforms, adjusting a waveform phase, or adjusting an acoustic lens coupled to a transducer of the array.

The control unit may be coupled to electrodes and configured to control electrical stimulation delivery via the electrodes for causing modulation of neural activity. The control unit determines a correlation between a set of electrical stimulation control parameters and a set of ultrasound waveform control parameters in response to the data, which may include determining a volume of tissue modulated by the ultrasound waveforms. Electrical stimulation control parameters may be identified in response to the data for delivering a neuromodulation therapy using electrical stimulation.

In various examples, the control unit may control the ultrasound transducer array to deliver ultrasound waveforms for causing modulation of neural tissue in a patient at multiple neural sites and/or using multiple ultrasound control parameters, perform a comparative analysis of the data acquired for each of the neural sites and/or control parameters, and identify a target site for delivering the neuromodulation therapy by a therapy delivery system in response to the comparative analysis, identify a trajectory for delivery of an implantable therapy delivery device in response to the comparative analysis and/or identify at least one therapy parameter to be used to deliver therapy by the therapy delivery system to the patient in response to the comparative analysis. The therapy delivery system may be configured to deliver electrical stimulation, ultrasound, and/or pharmacological agents and may be wholly external, wholly implantable, or include a combination of external and internal therapy delivery components.

In other examples, a method is disclosed for delivering, via an ultrasound transducer array comprising at least one ultrasound transducer and adapted for external application to a portion of a patient's body, ultrasound waveforms for causing modulation of neural tissue in a patient. The method may comprise acquiring data indicating a response to the modulation, analyzing the acquired data to determine correlation data between a response to the modulation and an ultrasound control parameter, and reporting the correlation data to enable identification of at least one therapy parameter to be used to deliver a neuromodulation therapy to the patient by a therapy delivery system, wherein at least one of acquiring, analyzing, and reporting is performed by a control unit.

The implantable therapy delivery system is a deep brain stimulation system, in one example, for treating symptoms of Parkinson's Disease or other diseases affecting the central nervous system. The therapy delivery system is configurable to deliver neuromodulation therapy using the identified therapy parameter. In other examples, the implantable delivery system may be capable of electrical stimulation delivery, pharmaceutical delivery, and/or ultrasound delivery for providing a neurostimulation therapy according to an identified therapy delivery parameter.

DETAILED DESCRIPTION

In the following description, references are made to illustrative embodiments. It is understood that other embodiments may be utilized without departing from the scope of the disclosure.

Figure 1A:
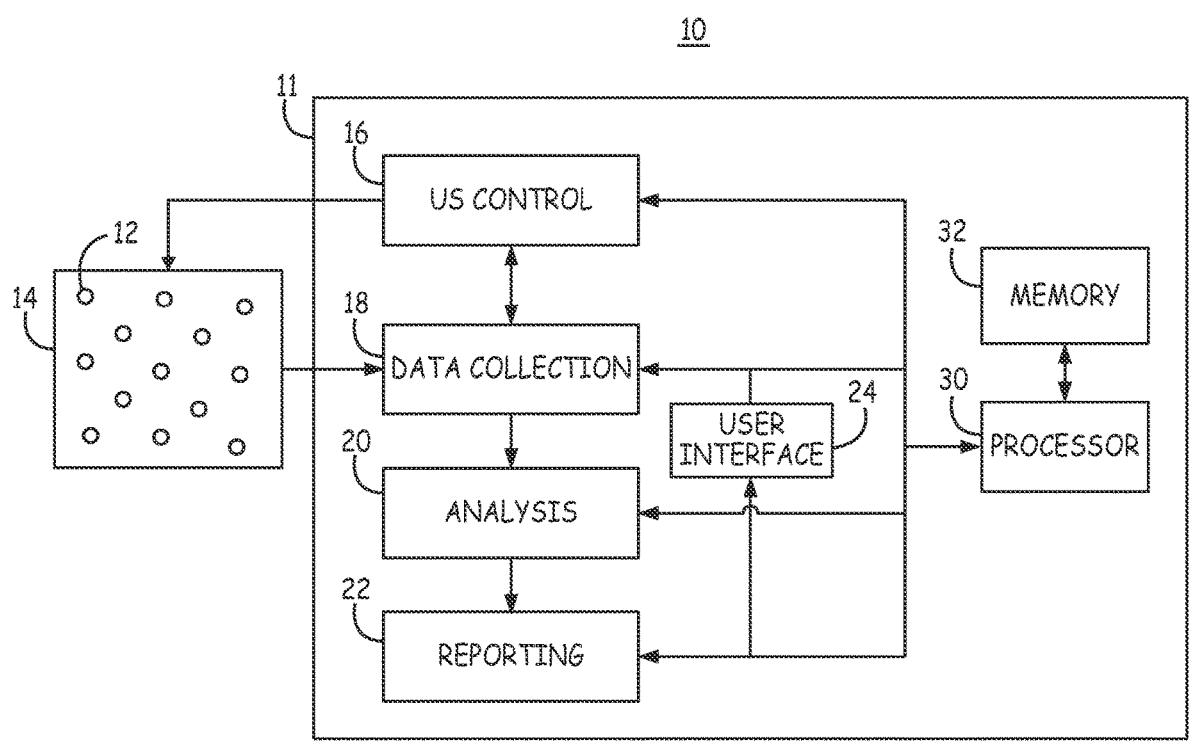
FIG. 1A is a schematic diagram of a diagnostic and therapy management system that uses low-intensity, focused ultrasound according to one embodiment.

FIG. 1A is a schematic diagram of a diagnostic and therapy management system 10 that uses low-intensity, focused ultrasound. Low-intensity, focused ultrasound pulses can be used to modulate neural tissue. Ultrasound is a cyclic sound pressure wave operating at frequencies above the auditory range of humans, e.g. above about 20 kHz. Ultrasound transducers can be positioned non-invasively and the focusing of pulsed signals at targeted or arbitrary locations can be adjusted by adjusting the location of the transducers emitting ultrasound pulses and the amplitude, duty cycle, frequency, shape, and phase of the pulses. In one embodiment, system 10 includes an ultrasound transducer array 12 coupled to a body-attachable or wearable substrate 14, and a system control unit 11 that includes an ultrasound (US) control unit 16 that controls the delivery of ultrasound pulses by transducer array 12, a data collection unit 18 that receives data input relating to a neural response to focused ultrasound pulses, a data analysis unit 20 for analyzing collected data and accumulating data correlating a response to neuromodulation and ultrasound neuromodulation control parameters, and reporting unit 22 that reports useful information determined from the data for potential diagnosis and treatment of a neural disorder, including identifying a neuromodulation therapy delivery parameter. Neuromodulation by focused ultrasound waves and by a subsequent therapy may include upregulation (activation or increased excitation), downregulation (blocking, inhibition or decreased excitation), synchronizing and/or desynchronizing of neural tissue.

US control unit 16, data collection unit 18, data analysis unit 20 and reporting unit 22 may be implemented in a single system control unit 11 for collecting data during an ultrasound neuromodulation study and for performing data analysis and reporting. Alternatively, units 16, 18, 20 and 22 may be implemented in system control unit 11 that is distributed across multiple devices or system components configured to cooperatively acquire, analyze and report data. Each of units 16 through 22 may include or share any one or more of a microprocessor 30 and memory 32 that execute one or more software or firmware programs, a controller, a digital signal processor (DSP), an application specific integrated circuit (ASIC), a field-programmable gate array (FPGA), or equivalent discrete or integrated logic circuitry, or other electronic circuitry or suitable components that provide the described functionality.

In the example shown in FIG. 1A, units 16 through 22 are shown residing at a single location, although this need not be the case. For instance, units 16 through 22 may each respectively reside on one or more different data processing systems that are communicatively coupled and located at different geographic locations. For instance, the reporting functionality may be located remotely from the control functionality ascribed to control unit 16. Moreover, the logic ascribed to each unit itself need not be located at a same geographic location or on a same data processing system. For instance, some of the functions ascribed to control unit 16, which are described in detail below, may be performed by logic residing on a first data processing platform and/or located at a first geographic location, and some others of the functions ascribed to control unit 16 may be performed by logic residing on a different data processing platform and/or located at a different location. Thus, many examples may be contemplated for the systems and methods associated with FIG. 1A. This is also the case for the other systems and methods described herein.

Units 16 through 22 may each include dedicated memory or share a memory structure 32 for storing neuromodulation control programs, data processing programs, data analysis and reporting parameters and other parameters and algorithms used for controlling the operations performed by system 10 as described herein. Memory 32 included in system 10 may include computer-readable instructions that, when executed by control 16, data collection 18, data analysis 20 or reporting unit 22 cause system 10 to perform various functions attributed throughout this disclosure to system 10. The computer-readable instructions may be encoded within the system memory, which may include computer-readable storage media such as any volatile, non-volatile, magnetic, optical, or electrical media, e.g., a random access memory (RAM), read-only memory (ROM), non-volatile RAM (NVRAM), electrically-erasable programmable ROM (EEPROM), flash memory, or any other digital media with the sole exception being a transitory propagating signal.

Substrate 14 may be configured as any wearable or body attachable substrate for carrying transducers 12 and maintaining transducers 12 in a stable position against a patient's skin during data collection. A coupling medium may be used to improve acoustical coupling between the transducers 12 and the patient's body. Transducers 12 may include an acoustic lens to focus emitted ultrasound waveforms or to improve focusing of the waveforms. When included, acoustic lenses may be passive or actively adjustable acoustic lenses where the focal parameters may be controlled by US control unit 16.

Depending on the particular diagnostic or therapy application, substrate 14 may be embodied as a cap or helmet for neuromodulation in the brain or as a strap, cuff, band or other structure for attachment to appropriate body locations to achieve neuromodulation at desired sites of the central and/or peripheral nervous system, e.g. along a patient's trunk or an extremity. In one embodiment, substrate 14 may be carried by an article of clothing. Substrate 14 may be securely attached to a patient using a variety of securing elements, which may include elastic materials, adhesive or adherent materials, buckles, or the like or may be designed to provide a snug, secure fit along or around a desired anatomical location.

The number, density and arrangement of transducers 12 may vary between applications. System 10 may be designed to operate with different transducer-substrate arrangements such that different sizes or shapes of substrate 14 having different numbers and patterns of transducers 12 can be coupled to US control unit 16. US control unit 16 can be adaptable to the number and arrangement of the transducers 12 in that transducer selection can be controlled according to the particular transducer number and arrangement being used and the particular disease application being evaluated.

The size and spacing of transducers 12 may vary depending upon the particular application of the techniques described herein. Transducers 12 may not consist of identical ultrasound emitters. Some transducers 12 may have different resonant frequencies, different focal depths and/or different relative alignments, e.g. to adjacent transducers, than other transducers 12.

US control unit 16 controls transducers 12 to emit therapeutic ultrasonic waveforms according to varying neuromodulation parameters that may include, but are not limited to, transducer selection, waveform shape, waveform amplitude, waveform frequency, pulse pattern or duty cycle, and waveform phase relative to waveforms delivered by one or more other transducers or other time reference. System 10 operates to deliver therapeutic ultrasound, i.e. ultrasound delivered to neurological tissue to modulate the neural activity to cause a beneficial neurological response. System 10 may additionally operate to deliver imaging ultrasound waveforms that are not necessarily intended to cause a therapeutic response. In some cases, emitted waveforms may be used for both causing neuromodulation and acquiring imaging data.

Control unit 16 may execute a programmed protocol that varies neuromodulation automatically throughout a data collection period. Additionally or alternatively, control unit 16 may receive feedback from data collection unit 18 and/or data analysis unit 20 to automatically control adjustment of neuromodulation parameters. For example, data collection unit 18 may signal control unit 16 when the data collection is complete for a particular combination of neuromodulation control parameters or signal that additional data collection time is needed. Data analysis unit 20 may analyze a structural image of a targeted neuromodulation site and provide feedback to control unit regarding focusing of the ultrasound waveforms, enabling the control unit 16 to adjust transducer selection and/or waveform phase, for example, to move a focal position of emitted waveforms.

Data collection unit 18 and/or analysis unit 20 may signal US control unit 16 if an adverse symptom, which may be a worsening symptom, a new symptom or side effect, is detected. Knowledge of the association of an adverse symptom or side effect with a particular target site and waveform control parameters provides information relating to disease state and can guide therapy management, e.g. avoidance of a target site or control parameters that result in adverse side effects. On the other hand, data collection 18 and/or analysis unit 20 may signal control unit 16 if a positive effect is being detected, e.g. an improvement in symptoms, and that fine tuning or optimization of a neuromodulation parameter should be executed. Optimization may include adjustment of the focusing of the waveforms within a target site, adjusting the volume of stimulated tissue, and adjusting the amplitude, frequency, duty cycle, or other control parameters to achieve an optimal effect.

Data collection unit 18 may include inputs for receiving automated data collection and user-entered data. Accordingly, system 10 may include a user interface 24 in wired or wireless communication with data collection unit 18 for receiving input from a patient or clinician relating to a neuromodulation response. User interface 24 may include a graphical user interface with a touch screen, key board, mouse or other pointing tool. A user may provide binary observations, such as a "yes" or "no" input relating to the presence or absence of symptoms or side effects or the worsening or improvement of symptoms or side effects. A user may additionally or alternatively provide a scaled response over a continuum of values, for example a rating of the presence of a symptom or side effect over a worst to best scale, which may be a numerical scale. A clinician may enter other physiological measurements in quantitative values.

The user input may be entered in user interface 24 as the clinician or patient observes or perceives the symptoms or side effects or a change therein as neuromodulation is delivered and control parameters are varied, with or without the user being aware of a change in a control parameter. Alternatively, at the end of a neuromodulation episode using a test set of control parameters, the user may be prompted for input before US control unit 16 adjusts one or more control parameters and initiates a next neuromodulation episode using a next set of test control parameters.

Additionally or alternatively, data collection module 18 may automatically acquire signals for measuring a physiological response to neuromodulation delivered while varying one or more control parameters. As will be described further herein, US control unit 16 may control transducers 12 to alternate between a transmission mode in which ultrasound pulses are emitted for modulation of a targeted neural site and a reception mode in which transducers 12 receive reflections of emitted waveforms. The reflections are used by data analysis unit 20 as feedback for focusing the ultrasound waveforms on a neural target and/or measuring a physiological response to the neuromodulation. Visualization of tissue being stimulated by ultrasound waveforms may be provided by the reporting module 22 through a display of a patient specific or clinical anatomical model or a representation of the nervous system or portions thereof.

Data collection unit 18 may additionally or alternatively receive input from other physiological monitoring or imaging sources, which may include but are not limited to, magnetic resonance imaging (MRI), functional MRI, positron emission tomography (PET), computed tomography (CT), electrocardiogram (ECG), electromyogram (EMG), accelerometer and electroencephalogram (EEG). Functional imaging, anatomical imaging, and/or electrophysiological measurements can be used by analysis unit 20 to identify a target site(s) and monitor a neuromodulation response.

Data analysis unit 20 receives data collected by data collection unit 18 for computing metrics of neuromodulation responses to the varied neuromodulation control parameters. Data analysis unit 20 may identify a set of control parameters resulting in a greatest reduction or improvement in symptoms, least side effects, and/or greatest physiological response at a targeted site, for example as evidenced by functional MRI, PET or electrophysiological signals. The volume of tissue stimulated by the focused ultrasonic waveforms at a target site may be computed to correlate target site size (i.e. volume) with waveform control parameters. The data analysis unit using metrics of neuromodulation responses is configured to analyze the acquired data to determine a correlation between a response to the modulation, e.g. change in symptoms, physiological measurement, affected target tissue volume, and one or more ultrasound control parameters. Data analysis unit 20 may be configured to aggregate data such that tissue volumes and targets affected by particular neuromodulation control parameters can be established within the patient and across patient populations.

Reporting unit 22 presents data analysis results to the user. Reporting unit 22 may operate in different reporting modes and may present data during data collection as well as after data collection is complete. For example, reporting unit 22 may include a display for presenting a two-dimensional or three-dimensional anatomical image during data collection with superimposed indicators of targeted neuromodulation sites, functional response at targeted sites or other monitored sites, and/or a computed volume of affected tissue at targeted sites.

Upon completing data collection and analysis, reporting unit 22 may present data analysis results in a graphical, tabular, or imaging format allowing comparisons of neuromodulation control parameters based on symptoms, side effects, targeted site volume, measured functional responses or other data of interest. Data may be presented as a three-dimensional volume display correlated statistically with neuromodulation outcome. A user interacting with interface 24 may be able to select data presentation formats, data content and other user preferences and toggle between windows of different data analysis results and comparisons and detailed and summary reports.

In some embodiments, reporting unit 22 may present a therapy planning guide in which targeted site(s) and control parameter settings are recommended based on data analysis results. The reporting module may be configured to report or display data relating to a correlation between an ultrasound control parameter and a neuromodulation response to enable identification of at least one therapy parameter to be used to deliver a neuromodulation therapy to the patient by an implantable system. The therapy parameter may be an identified target site resulting in positive therapeutic benefit or another control parameter as described further below.

Reporting unit 22 may include data storage and/or transfer capabilities, such that a patient file can be created for storing a report, including text and graphical data, and transferred to digital storage media, e.g. via a communication network, USB port or disc drive, flash memory or the like.

Figure 1B:
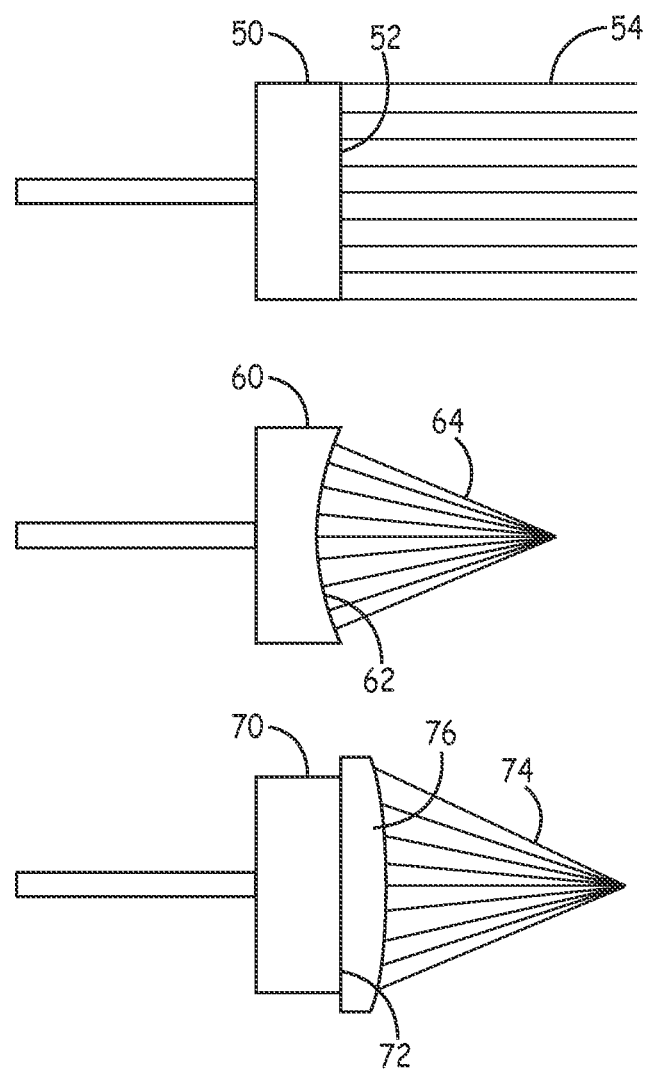
FIG. 1B depicts side views of various ultrasound transducer configurations that may be used in the system shown in FIG. 1A.

FIG. 1B depicts side views of various ultrasound transducer configurations that may be used in the system shown in FIG. 1A. Transducer 50 is shown having a flat acoustical surface 52 such that emitted waveforms 54 are unfocused. Transducer 60 includes a concave acoustical surface 62 emitting focused ultrasound waves 64. Transducer 70, having a flat acoustical surface 72, includes an acoustical lens 76 for focusing ultrasound waves 74. Transducers of the types illustrated by transducers 50, 60 and 70 or other types of transducers may be used solely or in any combination in a transducer array for delivering ultrasound neuromodulation. The waveforms emitted by a combination of transducers will be focused at a target site using control parameters such as phase relationships as further described below. As used herein, a transducer "array" refers to any n×n array, including a 1×1 array or a singular transducer. A transducer array is not limited to a linearly arranged array, or an array arranged in rows and columns, but may include, for example, a circular array, a random array or any other arrangement of transducers along a substrate.

Figure 2:
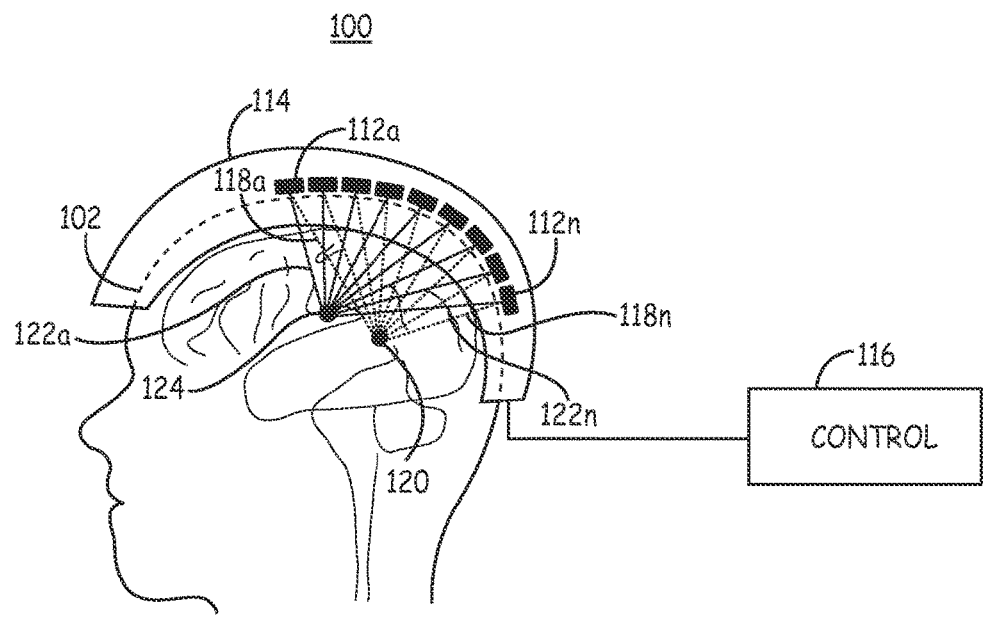
FIG. 2 is a schematic diagram of a therapeutic ultrasound delivery device that can be used in conjunction with the system shown in FIG. 1A.

FIG. 2 is a schematic diagram of a therapeutic ultrasound delivery device 100 that can be used in conjunction with system 10 shown in FIG. 1A. Device 100 is shown having a transducer substrate 114 in the form of a helmet or cap that may be adjustable for fitting externally along a patient's cranium 102. Substrate 114 carries multiple ultrasound transducers 112a through 112n, referred to collectively as transducer array 112. Transducers 112a through 112n may be embedded in or coated with an acoustical coupling medium to minimize signal losses between the transducer surfaces and the patient's skin surface. Transducers 112a-112n may or may not include an acoustic lens. When included, an acoustic lens associated with a particular transducer in array 112 may be embodied as an actively adjustable acoustic lens where the focal parameters may be controlled by control unit 16 in FIG. 1A or control unit 116 of FIG. 2.

Transducer array 112 is coupled to a control unit 116 for controlling ultrasound wave emission by array 112. Transducer array 112 and control unit 116 may generally correspond to transducer array 12 and control unit 11 shown in FIG. 1A. As shown in FIG. 1A, a transducer array 112 may also be coupled to a data collection unit (not shown in FIG. 2) for acquiring data signals from transducer array 112. The transducers included in array 112 are controllable individually. Control unit 116 may select transducers 112a through 112n one at a time or in any combination for emitting ultrasound waves.

Control unit 116 selectively controls which of transducers 112a through 112n are enabled for emitting ultrasound waveforms and which transducers 112a through 112n are not enabled or turned off. Control unit 116 controls the waveform parameters defining the waveforms emitted from each enabled transducer in array 112. The waveform control parameters include, but are not limited to, waveform shape, waveform amplitude, waveform frequency, duty cycle and the waveform phase. The phase may be defined with respect to another transducer waveform, for example a waveform generated by an adjacent transducer, a center transducer or end point transducer 112a or 112n, or another common time or clock reference.

In particular, the control unit 116 controls the waveform phase to select a therapy pathway for each of the individually emitting transducers 112a through 112n. For example, transducers 112a through 112n may be controlled to emit waveforms in a phase relationship that results in the waveforms being transmitted along therapy pathways 118a through 118n, focusing the emitted ultrasound energy from all of the selected emitting transducers 112a through 112n at a first target site 120. Control unit 116 may then adjust the phase relationship between transducers 112a through 112n to redirect the waveforms along therapy pathways 122a through 122n to focus the ultrasound energy at a different, second target site 124.

In this way, a multi-transducer array 112 can be controlled to emit and focus ultrasound energy for therapeutic benefit at one or more target sites. The volume and shape of the focal points 120 and 124, for example, will depend in part on the number of transducers and inter-transducer waveform phase relationships selected by control unit 116.

Control unit 116 can be configured to step through a programmed menu of target sites or along one or more known brain circuits for diagnostic and therapy management purposes as will be further described herein. Target sites may be selected one at a time in a sequential manner or selected two or more at time for simultaneous neuromodulation at more than one target site. A menu of target sites used by control unit 116 to select transducers 112a through 112n may include sites selected one at a time or in combination, in any desired order.

In some embodiments, control unit 116 controls array 112 to operate in a receiving mode for measuring reflections of ultrasound waves for use as feedback in focusing ultrasound energy on a target site and/or for measuring a functional response to neuromodulation. Control unit 116 may control array 112 to emit therapeutic waveforms and measure reflections of the therapeutic waveforms using the same transducer(s). Alternatively, control unit 116 controls array 112 to emit therapeutic waveforms and imaging waveforms using two different sets of waveform emission control parameters. Array 112 may be controlled to alternate between therapeutic and imaging waveform emission, in which different waveform control parameters define respective therapeutic waveforms and imaging waveforms. Emitted waveforms may have a frequency ranging between approximately 0.1 MHz and 20 MHz. In some embodiments, low frequency therapeutic waveforms may have a frequency in the lower range of approximately 0.1 MHz to 5 MHz and this frequency range may overlap or correspond to the frequency of imaging waveforms such that reflections of the therapeutic waveforms can be measured by system 10 for generating image data.

In other embodiments, higher frequency waveforms may be required to generate desired imaging data than a frequency used to deliver therapeutic waveforms. In this case, array 112 may be controlled to emit distinct therapy waveforms and imaging waveforms, which may be delivered simultaneously or in an alternating manner. The imaging waveforms may be delivered by selecting the same or different transducers 112a through 112n as the transducers selected for delivering therapeutic waveforms. The imaging waveforms may be less focused than therapy waveforms to obtain a larger view of an anatomical region or focused on a different site than a therapy target site for monitoring a functional response.

The reflections of the imaging waveforms are measured for generating image data. In some embodiments, the reflections of the therapeutic waveforms may be measured in addition to the reflections of the imaging waveforms for collecting data relating to a target site, relating to the therapy pathways 118a through 118n, 122a through 122n, and/or relating to a functional response to the therapeutic waveforms at the therapy target site or a different site.

A target therapy delivery site may be different than a target imaging site. The neuromodulation therapy may be delivered at a target site while functional imaging is performed at a monitoring site, i.e. a targeted imaging site, to measure a change in response to the therapy. For example, a response to neuromodulation may include a change in tissue density due to a blood flow change at the target therapy site or at a different monitoring site. Accordingly, control parameters for causing array 112 to emit waveforms for imaging may include transducer selection, waveform phase, or other parameters that influence focusing of the waveforms. The size of the monitoring site may be larger than the size of the target therapy delivery site, and the monitoring site may or may not include the target therapy delivery site. The focusing resolution(s) and target(s) for therapy delivery and monitoring sites can be defined separately in a menu of neuromodulation target sites to be tested. Array 112 is controlled to achieve therapy delivery at targeted site(s) and monitor for a response to therapy at imaging site(s) selected to correspond to an expected response to neuromodulation at the targeted site.

Array 112 may include dedicated therapy delivery transducers and dedicated imaging transducers in some examples. The imaging transducers may be controlled to operate simultaneously or in alternation with therapy delivery transducers for delivering therapy and collecting imaging data. As such, array 112 may include two or more sub-arrays, which may include one or more dedicated therapy delivery array(s) and one or more dedicated imaging array(s). The functionality of the transducers 112a through 112n, however, may be completely programmable and flexible as controlled by control unit 116.

Figure 3:
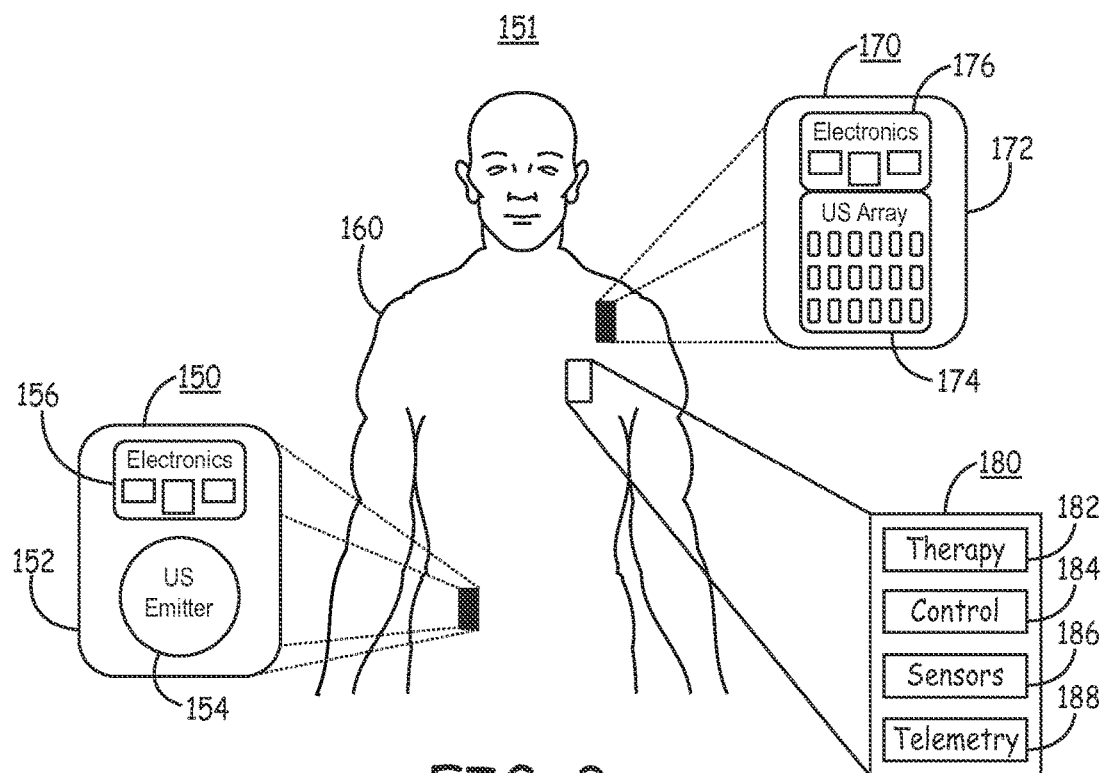
FIG. 3 is a schematic diagram of a neuromodulation trialing and therapy delivery system according to one embodiment.

FIG. 3 is a schematic diagram of a neuromodulation trialing and therapy delivery system according to one embodiment. The system 151 includes an external portion 150 and/or 170 and an implantable portion 180. The external portion is used to identify a therapy parameter used by the implantable portion 180 for delivering a chronic therapy to the patient. System 151 may be used to deliver therapeutic ultrasound waveforms to the central nervous system (CNS) and/or the peripheral nervous system (PNS). Two different embodiments of an external portion 150 and 170 are illustrated in FIG. 3 and are not necessarily to be used together though it is contemplated that one or more transducer arrays may be positioned on a patient 160 at various body locations to achieve CNS and/or PNS up regulation and/or down regulation. A transducer array may be positioned at any body location that enables the transducer(s) to emit waveforms focused on desired peripheral nervous system and/or central nervous system target site(s).

External devices 150 and 170 may be configured with light-weight arrays with a limited number of transducers to increase patient comfort. The locations depicted in FIG. 3 are merely illustrative. Target nerve sites may include the spinal cord, vagus nerve, sacral nerve, cranial nerves, sciatic nerve, intercostal nerves, or any other central nerve target or peripheral nerve branch.

An external device 150 is shown to include control circuitry ("electronics") 156 and a single ultrasound transducer (shown by way of example as "emitter") 154 carried by a substrate 152. Transducer 154 may only operate as an emitter in some embodiments and may operate as an emitter and receiver in other embodiments for both delivering a therapeutic waveform and receiving waveform reflections for acquiring data. Control circuitry 156 may be configured to perform all or a portion of the control operations corresponding to control unit 11 in FIG. 1A. For example, control circuitry 156 may enable transducer 154 to emit a waveform according to a selected amplitude, frequency and duty cycle. Control circuitry 156 may control transducer 154 to emit therapeutic waveforms under one set of control parameters and emit imaging waveforms under a second set of control parameters as well as receive reflections of the imaging waveforms and optionally the therapeutic waveforms.

External device 170 is shown to carry a transducer array 174 and control circuitry ("electronics") 176 on a substrate 172. Transducers in array 174 may be selected singly or in any combination and individually controlled as described above to focus emitted ultrasound energy at one or more targets sites. Energy may be focused at selected target sites sequentially or simultaneously, and ultrasound waveforms emitted by array 174 may be controlled for both neuromodulation and imaging as discussed above in conjunction with FIG. 2.

As discussed above, the size and spacing of transducers included in devices 100, 150, and 170 may vary between embodiments. Transducers may include different resonant frequencies, focal length, relative alignment and may or may not include acoustic lenses as described previously.

Implantable device 180 includes a therapy delivery module 182 for delivering a neuromodulation therapy, a control module 184 for controlling device functions, a sensor module 186 for detecting a need for therapy and/or monitoring a response to provide feedback in a closed or open loop manner for controlling the therapy, and a telemetry module 188 for transmitting data to an external device, which may be one of devices 150 and 170, and for receiving commands from a programmer.

Before device 180 is implanted, external device 150 and/or 170 is used to identify at least one therapy parameter to be used for delivering a neuromodulation therapy by implantable device 180. External device 150 and/or 170 may be used after implantation of device 180 to identify adjustments to the therapy to refine or optimize the therapy delivered by the implantable device 180. While a single implantable device is shown, it is recognized that one or more implantable devices and/or one or more external devices may be configured to deliver a chronic neuromodulation therapy to a patient using a therapy parameter identified through data collection and analysis using external device 150 and/or 170 or other external systems described herein. A chronic therapy may be a single mode or multi-modal therapy including electrical stimulation, ultrasound stimulation, and/or drug delivery delivered by any combination of one or more implantable devices 180 and/or external devices 150 and 170.

Implantable device 180 may be a miniaturized device that is injectable. An injectable device may be configured to be foldable or collapsible in a delivery tool to facilitate implantation in a minimally invasive procedure then unfold or expand upon deployment at an implant site. The therapy delivery module 182 may include electrodes, a drug or fluid delivery port, and/or an array of one or more ultrasound transducers. In some embodiments, the therapy delivery components of therapy delivery module 182 are incorporated in or along a housing of device 180. In other embodiments, a portion of the therapy delivery module 182 may extend from device 180, e.g. electrodes or ultrasound transducers carried by a lead or a drug delivery port at a distal end of a drug delivery catheter. For example, an ultrasound transducer array may be configured as an injectable array or an array that is expandable or unfoldable upon being deployed to a site and then coupled to device 180 via a lead tunneled between a therapy delivery site and an implant site of device 180.

Device 180 is configurable to deliver a therapy according to a parameter identified using an external portion of system 151. As further described herein, a therapy parameter identified using the external device 150 or 170 or any of the other external systems shown herein for neuromodulation during a trialing procedure may include a therapy delivery target site, a therapy delivery control parameter controlling electrical stimulation patterns, ultrasound stimulation patterns, and/or drug delivery rates and dosages, and/or a trajectory of an implantable therapy delivery component within patient 160.

Figure 4:
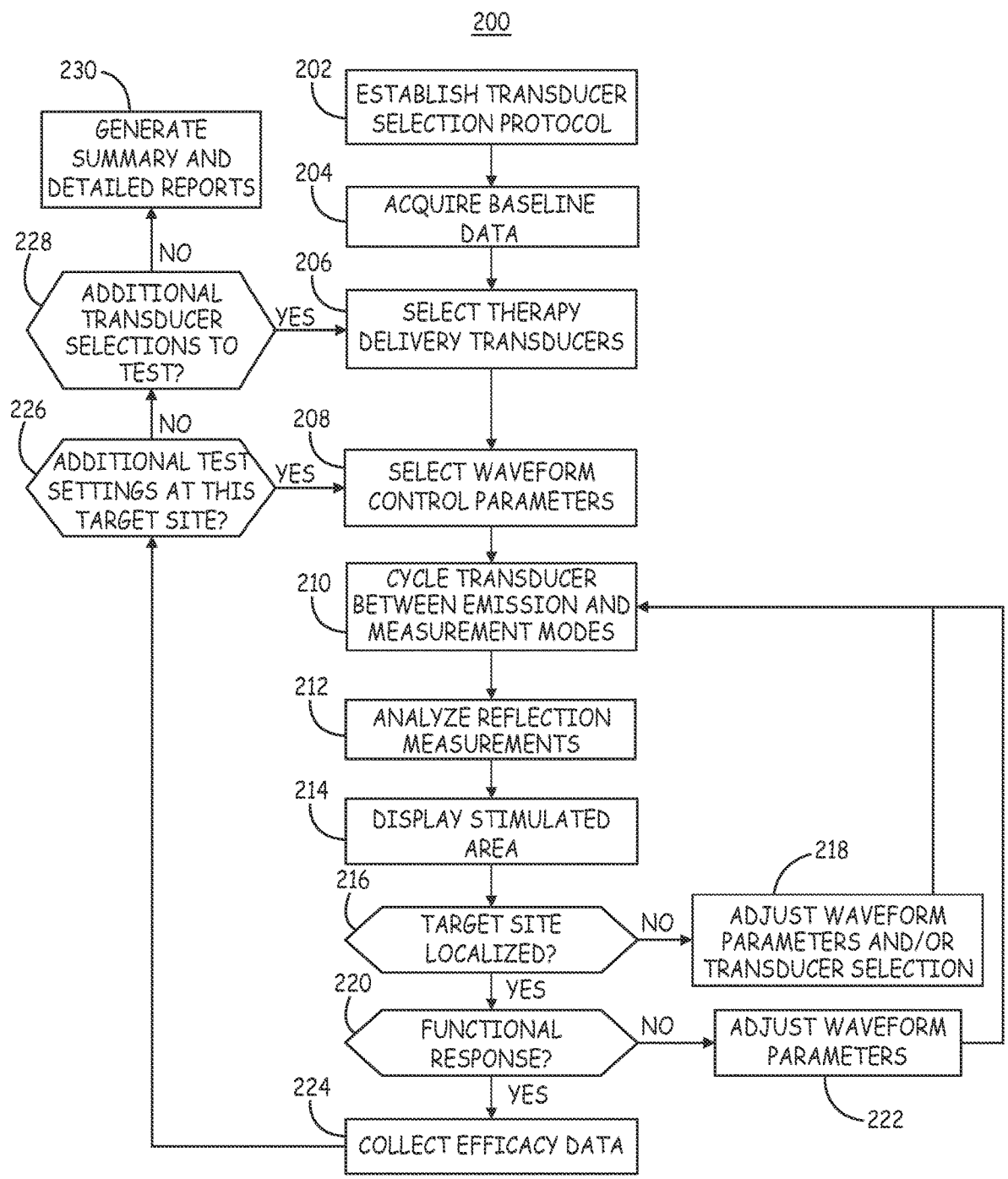
FIG. 4 is a flow chart of a method for operating the diagnostic and therapy management system of FIG. 1A according to one embodiment.

FIG. 4 is a flow chart 200 of a method for operating the diagnostic and therapy management system 10 according to one embodiment. Flow chart 200 is intended to illustrate the functional operation of the device, and should not be construed as reflective of a specific form of software or hardware necessary to practice the methods described. Methods described in conjunction with flow charts presented herein may be implemented in a system including a non-transitory, computer-readable medium that includes instructions for causing a programmable processor to carry out the methods described. A "non-transitory computer-readable medium" includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software and/or firmware modules, which may be executed by themselves or in combination with other software. In addition, some of the aspects of the method may be carried out in hardware, which may include one or more processors, micro sequencers, discrete digital and/or analog components, or any combination thereof, including any combination of hardware and software.

For brevity, each step of the method of FIG. 4 (as well as the other methods described herein) may be described as being performed by "control logic". In some cases, this control logic may be more specifically described as a particular control unit (e.g., control unit 16 or 116). In any case, it will be understood that this control logic or control unit may be any combination of firmware, hardware, and software according to any of the foregoing logic formats. It will be further understood that each of the steps described in the following paragraphs can be performed by different, or a same, set of such logic, than the control logic that performs a different step. In some cases, the control logic may comprise logic that is all at a same location. In other cases, the control logic used to perform a step may be at a different location compared to the control logic performing another step (e.g., two servers located at two different locations.) Thus it will be appreciated by those skilled in the art that many different examples of the method of FIG. 4, as well as the other methods described herein, are possible.

At block 202 of FIG. 4, a transducer selection protocol is established by the control unit 16. The transducer selection protocol defines the transducer combinations that will be tested during a test session and may define the order in which the combinations are tested. The transducer selection protocol may alternatively be defined as a target site protocol in which the desired target sites are defined, and control unit 16 operates to select transducers in array 12 to achieve ultrasound waveform focusing at the desired target sites.

The target site or transducer selection protocol may define or determine different combinations of transducers in array 12 to be tested to focus the ultrasound energy at different target sites and to determine the effects of different vectors through which the ultrasound energy passes to arrive at a target site. For example, different vectors may traverse different anatomical structures and tissue densities, such as bone versus soft tissue, which may cause variations in the focusing of the ultrasound waves at a target site.

Transducers in array 12 may be selected singly, in combinations of two or more, or in multi-transducer arrays that may include relatively larger numbers of transducers, e.g. 10 to 100 transducers or more, for testing neuromodulation effects at one or more target sites. Establishment of the transducer selection protocol at block 202 may therefore include storing in a programmable memory accessible by US control unit 16 one or more combinations of transducers to be tested during a diagnostic and therapy planning session. The transducer test combinations may be applied in a random order or in a predefined order, which may be prioritized based on an expected success rate, minimized energy, or other prioritization criterion. An expected success rate may be based on making a diagnosis in a time efficient manner or determining an efficacious therapy target site in a time efficient manner.

Establishment of the transducer selection protocol may be based on clinically known neural sites corresponding to various diseases associated with presenting patient symptoms. The protocol may be established to systematically test transducer combinations configured to focus the ultrasound energy at known sites associated with a highest incidence of a disease corresponding to the presenting patient symptoms first and progress to sites associated with progressively lower incidence of disease, for example.

A neuromodulation response to ultrasound waveforms can be resolved to a volume of tissue having a diameter as small as approximately 4 mm or less. Accordingly, transducer combinations may be selected to enable localization of the waveform energy within a particular neural structure, for example within a particular brain structure or within a particular location of a brain structure, for example the dorsal portion of the subthalamic nucleus (STN).

Transducer selection and waveform phase may affect the volume of tissue stimulated by neuromodulation. Accordingly, different transducer combinations and/or waveform phases may be included in the transducer selection protocol to stimulate different volumes of tissue at a target site, which may be useful in determining the extent of disease progression or severity. Transducer selection may be established to deliver therapeutic ultrasound energy at multiple target sites simultaneously or at different locations within a target site to determine which therapy delivery sites are associated with a change in patient symptoms or a monitored parameter, such a functional image change, which is indicative of therapeutic benefit.

In some cases, an established transducer selection protocol may include a single test transducer or target site selection. Waveform control parameters may be varied without varying transducer selection to test the efficacy of neuromodulation at one particular site. Focusing at the site may still be varied within bounds by varying waveform phase.

The transducer selection protocol may be established in response to manually entered data by a user using user interface 24. A user may enter a particular disease type or symptoms to enable control unit 16 to select from a menu of pre-programmed transducer selection protocols. Such protocols may be based on known centers or structures of the CNS or PNS associated with a suspected disease or presenting symptoms.

In some cases, the required transducer selection and other focusing parameters used by the US control unit 16 will be determined during the neuromodulation session through a search algorithm to arrive at the desired targeted sites, without using predefined transducer and other control parameter selections. Thus, in some cases the transducer selection protocol established at block 202 may include a systematic cycling through all, or a subset of all, of the available transducers to determine which transducers to activate to achieve desired stimulation results, and for identification of an optimal subset of transducers for achieving a desired result. Additionally or alternatively, the control parameter selection may be performed by cycling through all, or some subset of all, of the possible parameter possibilities to determine which parameters to utilize to achieve desired stimulation results.

As discussed above, establishment of the transducer selection protocol may be based on clinically known neural sites corresponding to various diseases associated with presenting patient symptoms. In some cases, selection of sites may be associated with identifying neural circuits know to be associated with various diseases or disease states. Such circuits may include one or more anatomical structures that are functionally related to one another in some manner. For instance, functionally-related anatomical structures exist within the brain. By using ultrasound to stimulate one or more structures of a known circuit and then determining therapeutic and/or side effects, which may include determining how stimulation affects other structures within the same or a different circuit, information may be gained concerning disease and/or disease state.

Before continuing, it is noted that in some cases, the steps of FIG. 4 may be rearranged, and in other cases, some steps may be omitted entirely, without departing from the scope of the disclosure. For instance, step 214 of displaying the stimulated area may be omitted in an example that omits a display screen. As another example, some of the selection steps for selecting operational parameters may be rearranged. Thus, FIG. 4 should be considered as illustrative only, and not limiting.

Figure 5:
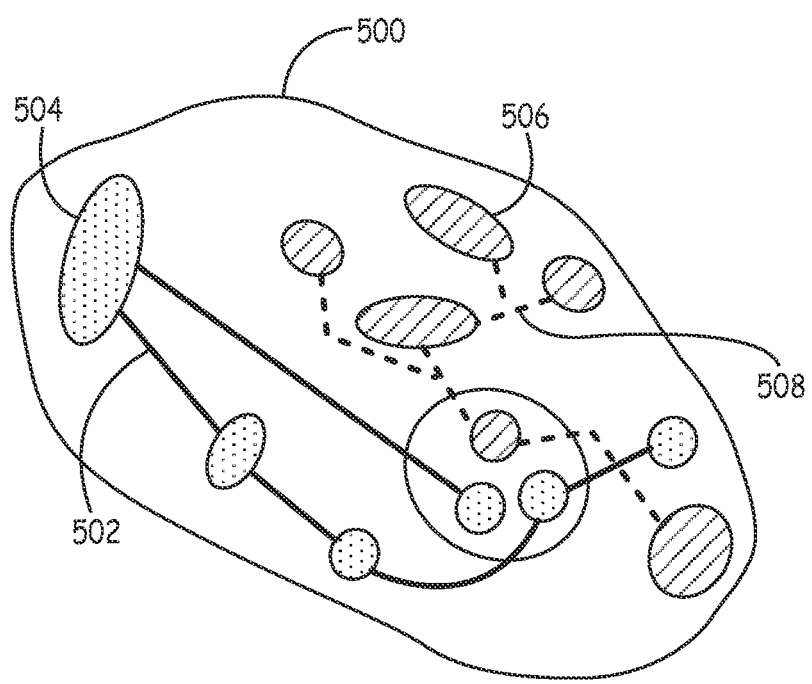
FIG. 5 is a schematic diagram of brain circuits in a patient's brain.

FIG. 5 is a schematic diagram of brain circuits in a patient's brain 500. A first brain circuit 502 shown by solid line links multiple brain structures 504. A second brain circuit 508 links brain structures 506. A transducer selection protocol may be defined to select transducers that will enable system 10 to focus neuromodulation waveforms on one or more structures 504, 506 of a respective brain circuit 502, 508 and along known neural pathways of these circuits. Neuromodulation at target sites along multiple brain circuits could be performed while acquiring functional imaging data to provide detailed diagnostic data. Example mechanisms for presenting a model of a brain network associated with a patient condition, as well as indicating functional relationship between the anatomical structures, are described in commonly-assigned U.S. Patent Publication 20110270348 entitled "Brain Stimulation Programming" which is incorporated herein by reference to the extent to which this reference is not inconsistent with the current disclosure.

Referring again to FIG. 4, at block 204, data collection unit 18 may acquire baseline data. Baseline data may include a two- or three-dimensional image of the patient's anatomy, a functional imaging measurement, user input relating to patient symptoms, or other physiological measurements that will be used to assess neuromodulation effects. In one embodiment, collection of baseline data includes using the selected transducer combination to obtain an ultrasound image of the patient's anatomy at a target site. As described above a transducer array may be used in a dual mode for both delivery of neuromodulation waveforms and for receiving waveform reflections, either of neuromodulation waveforms themselves and/or separately emitted imaging waveforms, for generating ultrasound image data. The ultrasound image data may be used for identifying the structures that the neuromodulation pulses must traverse to arrive at a target site, verifying focusing of waveforms at a target site, measuring a volume of tissue stimulated by the focused ultrasound waves, and measuring a functional response to neuromodulation at a target site. Accordingly, the baseline data may include obtaining image data using transducer array 12.

The first test transducer combination is selected at block 206 by control unit 16. Initial waveform control parameters are selected at block 208. Waveform control parameters include, but are not limited to, the amplitude, frequency, shape, duty cycle, and phase of the ultrasonic waveform emitted by each selected transducer. An initial set of waveform control parameters may be selected in part based on baseline data collected at block 204. For example, structures identified along a path traversed by the ultrasound beam(s) may require higher amplitude or frequency, i.e. greater intensity, to reach a target site. Initial pulse control parameters may be set at nominal settings or adjusted settings based on baseline data acquired at block 204. In some cases, waveform control parameters may include multiple sets of control parameters used in sequence or overlapping in time.

At block 210, the selected transducer combination is enabled by control unit 16 to emit ultrasonic waveforms according to the initial pulse control parameters. In one embodiment the transducer array 12 is cycled between a neuromodulation emission mode and a reflection measurement mode. In some embodiments, the same transducer(s) used to emit neuromodulation pulses are used to receive reflections of those pulses. Data collection unit 18 receives input signals corresponding to the reflected waves and converts the input signals to ultrasound image data.

The ultrasound image data is analyzed at block 212 by data analysis unit 20. Image data is optionally displayed at block 214 by reporting unit 22. Data analysis may be performed to determine if the ultrasound energy is focused on a target site as determined at block 216. This determination may be made by comparing the received image data to baseline image data of the patient's anatomy at the target site. If the received image data substantially matches the expected image data corresponding to the target site, the ultrasound energy is acceptably focused at the target site. If not, the transducer selection and/or waveform phase or other control parameters influencing focusing of the emitted waveforms may be adjusted at block 218. Analysis performed at block 212 may include analysis of target localization information from other sources, e.g., vibration or thermal sensitive MRI imaging, CT or PET scans, or other functional imaging or sensing.

In some embodiments, imaging data or other physiological measurements may be used by US control module 16 in closed-loop feedback control of the US transducers. Imaging or other acquired data may be used in adjusting transducer control, i.e. transducer selection and/or waveform control parameters. For example, patient movement causing a change in relative position between the ultrasound transducer array and a target site may be detected by analysis of the imaging data and this detection may be used by US control 16 to adjust the transducer selection or focusing to maintain neuromodulation at a desired target. In another example, the imaging data may be analyzed to detect an affected volume of tissue and the results of the analysis may be used in closed-loop feedback control by US control 16 to adjust the transducer selection, focusing and/or other ultrasound waveform parameters.

If the ultrasound energy is confirmed to be focused at the desired target site at block 216, a functional response may be measured at block 220. A functional response may be measured based on a change in measured reflections, e.g. due to a change in blood flow at the target site or another site expected to be affected by neuromodulation at the target site and present a functional change. If a functional response is not detected, the waveform control parameters may be adjusted at block 222 to achieve a neuromodulation response. For example, the amplitude, frequency and/or duty cycle of the emitted ultrasound may be increased.

If the target site and a functional response are confirmed at block 220, efficacy data may be acquired at block 224 by data collection unit 18. Efficacy data may include user entered data corresponding to patient symptoms or side effects. Efficacy data may include measuring additional physiological signals, such as electrophysiology signals, or acquiring additional functional imaging data, such as PET or CT scans or functional MRI data. Efficacy data may include the ultrasound reflection measurements used to obtain functional image data correlated to a response at the neuromodulation target site.

Various types of signals may be used to determine efficacy data. For instance, in the case of brain functionality, it is generally thought that the activation of numerous neurons is necessary to carry out each brain function. Moreover, for various areas of the brain, many of the neurons in one or more areas of the brain will depolarize, sometimes in synchrony, in an effort to carry out a function supported by the one or more areas. The presence or absence of depolarization, as well as relative timing of depolarization, can be measured to analyze disease and disease state.

The activation of neurons can be measured as a bioelectrical signal, such as a local field potential (LFP), electroencephalogram (EEG), magneto encephalography (MEG), and/or electrocorticogram (ECoG) signal, among other measurement techniques. Certain neurological and psychiatric disorders, including injury, epilepsy, and movement disorders, can be characterized by deficits in normal bioelectrical patterns and/or the presence of abnormal bioelectrical patterns.

A biomarker, as referred to herein, is a characteristic of one or more bioelectrical signals that is indicative of a particular patient state and/or particular neural activity. Various patient states may include brain states such as pre-seizure, ictal, seizure, tremor, dystonia, pain, mood (e.g., depression, obsessive compulsive disorder), active, overactive, sub-active, and intention state, among other states. In the case of a Parkinson's disease patient, beta frequency range bioelectrical oscillations may be associated with the occurrence of movement disorders symptoms while gamma frequency range bioelectrical oscillations may be associated with the absence or improvement in the occurrence of movement disorders symptoms. The presence of such bioelectrical signal characteristics as biomarkers may indicate patient tremor or non-tremor states. In the case of epilepsy, abnormal levels of beta frequency range bioelectrical oscillations may be present before and/or during a seizure patient state. In some cases, a biomarker can relate to connecting neural activity in one area of the brain to neural activity in a different area of the brain, such as correlating beta frequency band activity from a first brain area (e.g., the basal ganglia) to neural activity from a second brain area.

Signals of the types described above can be measured and analyzed in the time or frequency domain. Examples of various chopper amplifier circuits and measurement techniques that may be suitable for, or adapted to, collecting data and measuring responses to ultrasound modulation, as well as frequency selective monitoring and other circuitry and techniques applicable to the current subject matter, are described in commonly-assigned U.S. Pat. No. 7,385,443 issued on Jan. 10, 2008; U.S. Pat. Pub. No. 2009/0082829 filed on Oct. 16, 2007; and U.S. Pat. Pub. No. 2009/0082691 filed on Sep. 25, 2008, each of which are incorporated herein by reference to the extent to which these disclosures are not inconsistent with the current disclosure.

Collecting efficacy data may involve using the data to determine a patient state. For instance, it may be desirable to use collected signals to determine whether the delivery of ultrasonic waveforms to a particular brain structure or brain circuit promoted or inhibited a certain state, such as a seizure state. This type of determination may be useful in diagnosing a patient condition (e.g., epilepsy, Parkinson's disease, etc.) or determining the extent of that condition. Additional examples of patient states may involve a state associated with a lower amount of power exhibited in beta frequency range oscillations and/or a larger amount of power exhibited in the gamma frequency range oscillations. Examples of collecting data and using the data to classify patient states are described in commonly-assigned U.S. Ser. No. 13/589,270 filed Aug. 20, 2012, which is incorporated herein by reference to the extent to which this disclosure is not inconsistent with the current disclosure.

Other means of data collection may be utilized to gather efficacy data. For instance, one or more other types of external sensors may be coupled to, held by, or otherwise placed in contact with, a patient during delivery of the ultrasound energy to measure a physiologic response to the energy delivery. As a specific example, a device carrying one or more accelerometers, gyroscopes or other sensors that may be used to measure a patient's body position and body motion may be affixed to, or otherwise carried by, the patient while the ultrasound energy is being delivered. Such sensors may be used to detect an increase or reduction in tremor as a result of ultrasound delivered to one or more target sites of the brain. Other external sensors that may be used instead of, or in addition to, motion/activity sensors for measuring physiologic responses of the patient to ultrasound energy delivery may include, but are not limited to, blood pressure sensors (e.g., blood pressure cuffs), other pressure sensors, thermal imaging sensors, heart rate monitors, and external glucose monitors.

In some examples, the data collection may involve analyzing a patient's ability to perform a task, such as a task that involves motor coordination, to determine how the patient is responding to the delivery of ultrasound energy. Some type of scoring or other evaluating mechanism may be employed to determine the effects of the energy delivery on the ability to perform the task. Scoring may include patient self-scoring, clinician scoring, and/or automated scoring. For instance, an automated scoring system may assign a score to a patient's ability to align a tip of a stylus with designated targets on a pressure-sensitive display of a user input device while the ultrasound energy is being delivered. As another example, the patient or clinician may assign a score based on a perceived ease or proficiency with which a task was completed. In some cases, scores may alternatively or additionally be assigned to other types of patient responses besides motor responses. For example, a patient may be rated on an ability to respond verbally or cognitively to a request.

As discussed above, data collection can also involve gathering patient-reported sensory information or mood-related information while ultrasound energy is being delivered. For instance, the patient may report feeling "light-headed" or "seeing stars" while energy is delivered to a particular target site. The patient may report a mood-related feeling invoked by the delivered ultrasound energy ("happy") or some other type of sensation or response. This information may be recorded for use in evaluating energy delivery at that target site.

After collecting any additionally desired efficacy data and optionally using that data to determine a patient state, the ultrasound waveforms may be adjusted to alter the intensity delivered at the same target site. If additional waveform control parameter test settings are to be applied for the same target site, as determined at block 226, the next set of waveform control parameters is selected at block 208. Blocks 210 through 224 may be repeated for multiple combinations of waveform control parameters, e.g., different amplitude, waveform shape, frequency and duty cycle, while maintaining focus of the waveform energy at the same target site.

Ultrasonic stimulation can be used to inhibit or aggravate symptoms of various diseases. Both of these observations can be used to diagnose a condition and to determine a likely efficacious treatment. For instance, in some applications, non-destructive, high-intensity ultrasound is focused at a target site to temporarily disrupt neuronal activity at the site to determine if a symptom disappears. In other applications, the ultrasound intensity may be varied by varying amplitude, waveform shape, frequency and duty cycle to acquire functional imaging data and efficacy data corresponding to disrupting or down regulating neuronal activity at a target site and activating or up regulating neuronal activity at that target site. In other examples, the effect of blocking neuronal conduction by delivering ultrasound stimulation at one site and simultaneously increasing neuronal activation at another site by ultrasound stimulation may be evaluated.

In still other examples, the ultrasonic stimulation may be used to aggravate symptoms (e.g., promote a seizure state) to further allow for diagnosing a disease or evaluating a disease state. Aggravation of a disease state may further be used to determine a potential location for implantation of an electrode or to determine efficacious parameters, as will be discussed further below.

After applying all desired waveform control parameter test settings, if additional transducer selections are to be tested, as determined at block 228, the process returns to block 206 to select the next transducer combination. A different combination of transducers may be selected for focusing ultrasound energy at the same target site. A different transducer combination may provide efficacious neuromodulation at the same target site using less energy, e.g. due to lower energy loss as the ultrasound beam traverses other anatomical structures along a therapy pathway to the target site. A different transducer combination may result in reduced or no side effects due to a change in the pathway traversed to the target site. For example, if the patient is being evaluated for DBS or drug delivery, possible delivery pathways of a therapy delivery device such as a DBS lead or a drug delivery catheter could be targeted to determine possible side effects associated with traversing a potential lead/catheter pathway. Specifically, transducers may be selected to ultrasonically stimulate each point along a potential lead or catheter delivery pathway so that potential side effects associated with the pathway may be identified. In this manner, a delivery trajectory associated with a minimal number of side effects may be selected.

Undesired side effects such as pain or discomfort, tremor, loss of speech or other function, unintended up regulation or down regulation of non-targeted sites, or sensation of stimulation at non-targeted sites may be minimized through transducer selection and/or waveform control parameters. Accordingly, multiple combinations of transducers and/or waveform control parameter settings may be tested for a target site, as controlled at block 226, to collect data for identifying optimal neuromodulation therapy delivery parameters for that site, which may include parameters associated with electrical stimulation delivered to that target site.

Additionally or alternatively, different transducer combinations may be selected at block 228 for targeting a different site or for altering the location of energy focus within a target site. The efficacy of stimulating different targets in reducing symptoms may be compared. For example, a patient suffering from Parkinson's disease may undergo an evaluation to compare the potential benefits of DBS for reducing symptoms associated with Parkinson's disease, such as tremor, rigidity, or bradykinesia/akinesia, at different sites and/or circuits in the brain by focusing ultrasound energy at different target therapy sites and/or brain circuits.

Example target therapy sites for Parkinson's disease related symptoms or dystonia include, but are not limited to, the subthalamic nucleus (STN) and the globus pallidus (GPi). These target sites, or specific locations within these target sites, may be compared to determine the most effective stimulation site for reducing symptoms without unwanted side effects. Identification of an optimal therapy delivery site can be used to guide subsequent electrode lead placement to deliver electrical energy to the brain or to guide drug delivery catheters for delivering a substance to the tissue. In this manner, verification of the efficacy of electrical neuromodulation in reducing symptoms can be performed non-invasively using ultrasonic modulation prior to performing invasive surgery for implanting a DBS electrode. The path of delivery of an electrical lead can be evaluated to determine if it may be associated with any negative effects. Similarly, the effects of implanting a drug delivery catheter at a certain site and/or along a particular trajectory may be determined before the surgery is performed.

Among other conditions that may be evaluated for diagnosis and DBS therapy management is non-Parkinson's tremor. An example target site for non-Parkinson's tremor may be the ventrointermediate nucleus (VIN) of the thalamus. Still other conditions that may be evaluated according to the disclosed mechanisms include chronic pain, depression or other mental illness, epilepsy, obsessive/compulsive disorder, Tourette syndrome, post-traumatic brain injury, phantom limb pain, obesity, dystonia, essential tremor, MS tremor, psychogenic movement disorder, addiction, other neurological disorders and cochlear disease.

Localization of the focused energy at different sites within a brain structure, such as different sites within the thalamus, can be compared by collecting efficacy data for multiple locations, e.g., lateral vs. medial within a target site. Neuromodulation at multiple locations within a target site or different treatment volumes within the target site may be tested by varying the transducer selection and/or waveform control parameters. In some cases, multiple target sites may be targeted simultaneously. For example, efficacy data may be collected for comparisons between one or more single targets and one or more combinations of dual targets.

Knowledge of target sites that result in aggravation of symptoms may be as useful as knowledge of target sites that alleviate symptoms for diagnostic and therapy planning purposes. In some cases, the sites that are determined to result in aggravation of symptoms may become the target of surgery (e.g., resective surgery for epilepsy) or may be used as the target for electrical stimulation therapy or drug delivery. Ultrasonic stimulation of a particular site may further be used to determine the likely side effects of removal of a tumor. Stimulation of particular nerve targets may also be used to determine nerve integrity, as may be useful when performing surgeries such as spinal surgeries.

After collecting efficacy data for all desired transducer combination selections and waveform control parameters, data analysis unit 20 and reporting unit 22 are enabled to generate detailed and summary reports at block 230. Detailed reports may include data and measurements corresponding to each target site tested, such as functional imaging changes, user-entered responses, electrophysiological data, patient response scores, other sensor data, and so on. A summary report may list a recommended therapy delivery site(s) and corresponding waveform control parameters based on a greatest reduction in symptoms with least side effects and/or optimized response evidenced by functional imaging and/or other data.

The data analysis unit 20 may perform analytical or predictive modeling to identify control parameter selection reported by reporting unit 22. Data analysis unit 20 may utilize patient-specific data accumulated by data collection unit and stored in memory 32 and/or aggregate outcomes to parameter and transducer selection stored in historical data sets in memory 32, which may include patient-specific data sets and/or empirical data sets acquired from a population of patients. For example, data analysis unit 20 may reference a historical data set relating to a population of patients having a common disease state or set of symptoms and/or common physiognomy which identifies efficacious settings or ranges of settings for the patient population.

The report may include an optimal subset of transducers for use in a chronic therapy when an implantable or wearable ultrasound delivery device is to be used for delivering a chronic ultrasound neuromodulation therapy. An optimal subset may be determined analytically from the data collected, by predicting the effect of using various subsets or iteratively by testing various subsets, or a combination of both analytical and iterative testing.

Identification of a therapy target site may be achieved through direct testing of neuromodulation at that target site, but may alternatively be achieved through extrapolation of results of testing at other target sites. For example, positive results from neuromodulation at one site may be well correlated with positive results from neuromodulation at another site. Accordingly, a target site may be identified and reported that was not necessarily tested directly during the assessment performed by system 10, but is identified through correlation of test results and expected response(s) at another site(s). This correlation may relate ultrasound neuromodulation at a given site to a different mode of neuromodulation at a different site, e.g. electrical stimulation at a different site. Identification through indirect testing can be beneficial when an ultrasound modulation site using the external system 10 and a therapy target site using an implantable device have different accessibility.

While the examples of FIG. 5 primarily focus on the brain as the target, it will be understood that some or all of the techniques described herein may be applied to any other area of the anatomy that may be the target of an electrical stimulation therapy, an ultrasound therapy, a drug delivery therapy, or any combination thereof. Such therapies may be delivered acutely or chronically. A chronic therapy is a therapy used for more than one day, for example, and may be delivered using external and/or implantable therapy delivery devices. Targets for acute or chronic ultrasound stimulation therapy, and for therapy planning using non-invasive or minimally invasive ultrasonic modulation, may include but are not limited to, the following: spinal nerves for back pain, intercostal nerves for mastectomy pain, sciatic nerve for muscular constriction, supra/suborbital/infraorbital nerves and trigeminal nerve for facial pain, cranial nerves for cervical pain, median nerve for carpal tunnel, cluneal/iliohypogastric/lateral femoral nerves for pain associated with iliac bone crest harvest, ilioinguinal and iliohypogastric for herniorrhaphy pain, vagus nerve for vagus nerve stimulation for treating epilepsy, hypertension and depression and occipital nerves for chronic migraine. Urinary frequency and urgency, fecal incontinence, chronic pelvic pain, painful bladder syndrome, interstitial cystitis, chronic prostatitis, and sexual dysfunction may be treated with any combination of stimulation to sacral nerves, pudendal nerve and its branches, tibial nerve and its branches, dorsal nerve of clitoris for females, and dorsal nerve of penis for males. In some examples, ultrasonic stimulation may be delivered to excite nerves for exercising muscles following spinal cord injury. Ultrasonic neuromodulation may include upregulation or activation, downregulation or blocking of a targeted nerve, synchronizing and/or desynchronizing neural tissue. Ultrasonic neuromodulation may be combined with electrical, pharmaceutical or other neuromodulation techniques, and may target a different modulation site. For example ultrasonic modulation of a peripheral nerve site may be combined with electrical stimulation of a central nervous system site or vice versa.

Figure 6:
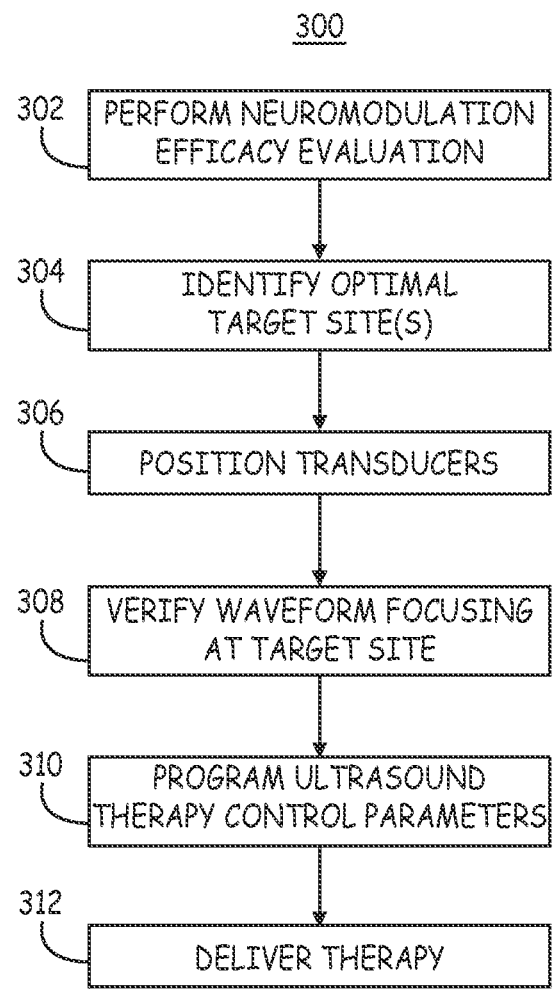
FIG. 6 is a flow chart of a method for managing a neuromodulation therapy in a patient.

FIG. 6 is a flow chart 300 of a method for managing a neuromodulation therapy in a patient. At block 302, an evaluation of the efficacy of neuromodulation for treating a patient condition is performed according to the methods described in conjunction with FIG. 5, such methods being applicable to targets other than just the brain as described above. Based on generated reports, one or more optimal neuromodulation target sites are identified at block 304 for achieving therapeutic benefit. At block 306, ultrasound transducers are positioned to provide chronic neuromodulation therapy. The ultrasound transducers may be carried by a wearable or body-attachable substrate as generally described previously herein. The number of transducers used in an array for therapy delivery may be fewer in number than the number of transducers included in an array for diagnostic and therapy planning purposes. The number of transducers used for chronic therapy delivery is selected based on the requirements for focusing the ultrasound waveforms at the identified target site(s). Positioning of the transducers will be based on the therapy delivery system being used. Targets may include, but are not limited to, those targets listed above.

Ultrasonic waveforms and parameters may be varied to activate targets at different sites and different depths/locations within the patient's body. Multiple ultrasound waveform emission modalities may be cycled by varying the ultrasonic parameters. The multiple modalities may be delivered sequentially or simultaneously to create a synergistic effect in the same or different anatomical sites.

The system may be a wholly external system. In some cases, transducers may be implanted beneath the skin using transcutaneous leads for coupling the transducers to control circuitry and a power source. In other embodiments, a wholly implantable system may be used. For DBS applications, ultrasound transducers may be positioned along desired points on the cranium, cutaneously or subcutaneously. For subcutaneous implantation, transducers may be anchored to the skull or positioned in small cavities formed in the skull, or implanted beneath the skull. Ultrasound arrays may be implanted surgically or percutaneously. In some instances the array may unfold after implantation to increase surface area. More than one array may be implanted. For peripheral nerve applications, transducers may be implanted in the subcutaneous or intramuscular layers, or any area that has sufficient vicinity to a stimulation target. In some cases, a transducer may be of a size and shape that allows it to be injected at a target location. As discussed above, a transducer may be designed to unfold or otherwise expand after being injected or placed in some other manner at the target location at which the transducer interfaces with the tissue.

After positioning the transducers at the desired locations at block 306, verification of focused emitted waveforms at the identified target site(s) may be performed at block 308 using any of the same techniques described in conjunction with FIG. 4. Adjustment of the transducer locations and/or relative waveform phases may be performed as needed to achieve focusing of ultrasound energy at desired target site(s) and a stimulated tissue volume.

At block 310, the therapy control parameters are programmed in a therapy control unit according to optimal waveform parameters identified in the efficacy evaluation, e.g. as provided in the summary report. The amplitude, frequency, and duty cycle may be programmed in addition to waveform phase to provide therapeutically effective neuromodulation at the target site(s). The therapy is delivered according to the programmed control parameters at block 312.

Figure 7:
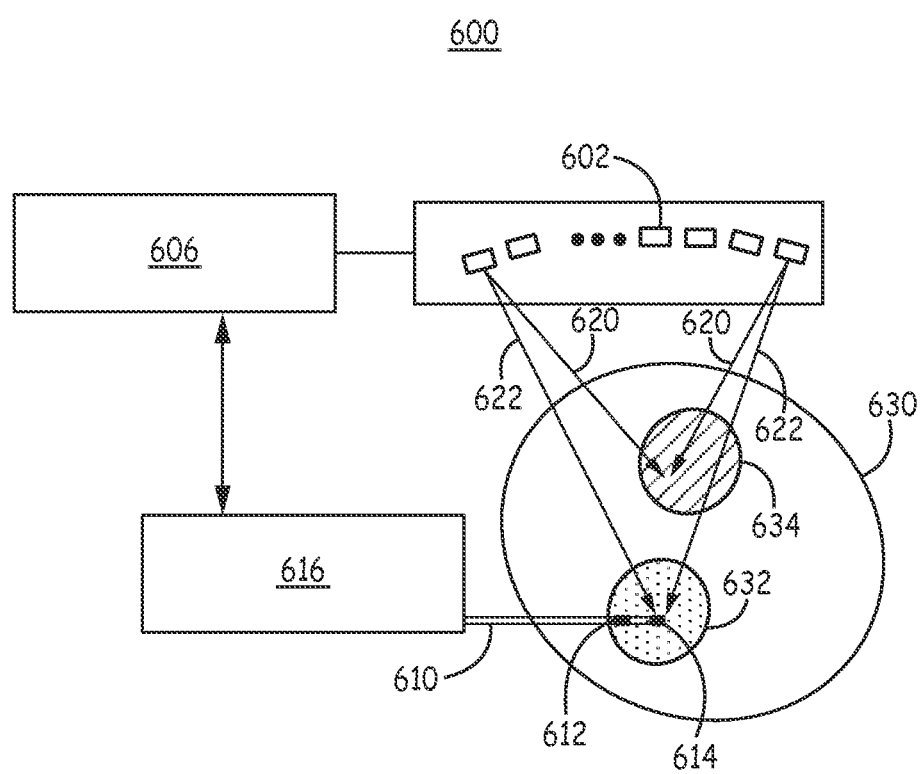
FIG. 7 is a schematic diagram of a diagnostic and therapy management system according to another embodiment.

FIG. 7 is a schematic diagram of a diagnostic and therapy management system according to another embodiment. In some cases, a patient may already have an electrical stimulation lead and electrodes (or a leadless device incorporating electrodes along a device housing) implanted for delivering an electrical neuromodulation therapy, such as DBS, spinal cord stimulation, vagus nerve stimulation or other PNS. The therapy may become less effective over time due to disease progression, changes in prescribed medications, or other factors. Accordingly, it may be desirable to identify new target sites or optimal neuromodulation parameters for delivering the therapy.

In FIG. 7, an electrical lead 610 is shown carrying an anode electrode 614 and cathode electrode 612 positioned in a target site 632 of a neural structure 630. It is recognized that numerous lead and electrode configurations may be used, including one or more leads carrying any number of electrodes arranged according to the needs for a particular patient and therapy delivery application. Lead 610 is electrically coupled to an electrical neuromodulation control unit 616. Control unit 616 includes a pulse generator for generating electrical pulses delivered by electrodes 612 and 614 and a therapy control unit for controlling the pulse generator to deliver electrical pulses according to a prescribed therapy. Control unit 616 additionally includes a sensing unit for acquiring electrical signals from electrodes 612 and 614 in some embodiments. Examples of systems for delivering electrical neuromodulation are generally disclosed in U.S. Pat. No. 6,484,059 (Gielen), U.S. Pat. No. 8,032,224 (Miesel, et al.), U.S. Pat. No. 8,204,607 (Rooney et al.), and U.S. Publication No. 2002/0198572 (Weiner), all of which are hereby incorporated herein by reference to the extent to which these disclosures are not inconsistent with the current disclosure.

An ultrasound transducer array 602 is positioned to deliver ultrasound neuromodulation in structure 630. Array 602 is coupled to an ultrasound control unit 606 which controls delivery of ultrasound waveforms via array 602. While array 602 appears as a one-dimensional array in FIG. 7, it is understood that array 602 may be a circular, concentric, rectangular or other two-dimensional array. Control unit 606 may additionally include a data collection unit, data analysis unit, and reporting unit as generally described in conjunction with FIG. 1A.

Control units 606 and 616 may optionally be communicatively coupled such that control of electrical neuromodulation and/or electrical sensing via electrodes 612 and 614 and control of ultrasonic neuromodulation and/or ultrasound imaging via array 602 may be cooperatively controlled by units 606 and 616 to deliver neuromodulation and acquire data for identifying new therapy target sites and/or optimal neuromodulation control parameters.

In addition to imaging data that may be collected via array 602 in response to delivery of therapeutic ultrasound neuromodulation, electrodes 612 and 614 may be used to measure an electrical response for data collection and analysis. Accordingly, control units 606 and 616 may operate cooperatively to acquire ultrasound imaging data, electrical signal data according to various types of signals described herein, other imaging data (e.g. MRI, functional MRI, PET, CT, etc.) and/or user-entered data for evaluating the efficacy of neuromodulation therapy delivered at varying target sites and/or therapy delivery control parameters. In this manner, ultrasonic stimulation may be used to identify additional stimulation sites and/or to modify the current target site. As one specific example, electrical stimulation may be delivered to a first hemisphere of a patient's brain. Ultrasound stimulation may be utilized to determine that the patient may benefit from receipt of stimulation at an additional target location within the second hemisphere of the patient's brain. This determination may be made without performing surgery. Once such a determination is performed, one or more additional electrodes may then be positioned at this additional target so the patient will receive electrical stimulation therapy in both hemispheres of the brains.

As mentioned previously, a neuromodulation therapy may include electrical stimulation at a target site, delivery of a pharmaceutical agent at a target site, and/or ultrasound modulation at a target site. As such, the lead 610 may alternatively be embodied as, or include, a drug delivery catheter and/or an ultrasound transducer array. An implantable therapy delivery system, including a control unit and a therapy delivery module, e.g. control unit 616 and lead 610 with electrodes 612 and 614 as shown in FIG. 7, may be configured to deliver neuromodulation therapy according to a therapy control parameter identified by the external ultrasound modulation system including control unit 606 and transducer array 602.

In some embodiments, the implantable therapy delivery system may already be implanted and present during analysis performed by the external system and in other embodiments, the external system is used as a trialing system to identify a patient who can benefit from neuromodulation therapy and the implantable system is selected and configured to operate using a therapy parameter identified by the trialing system.

Figure 8:
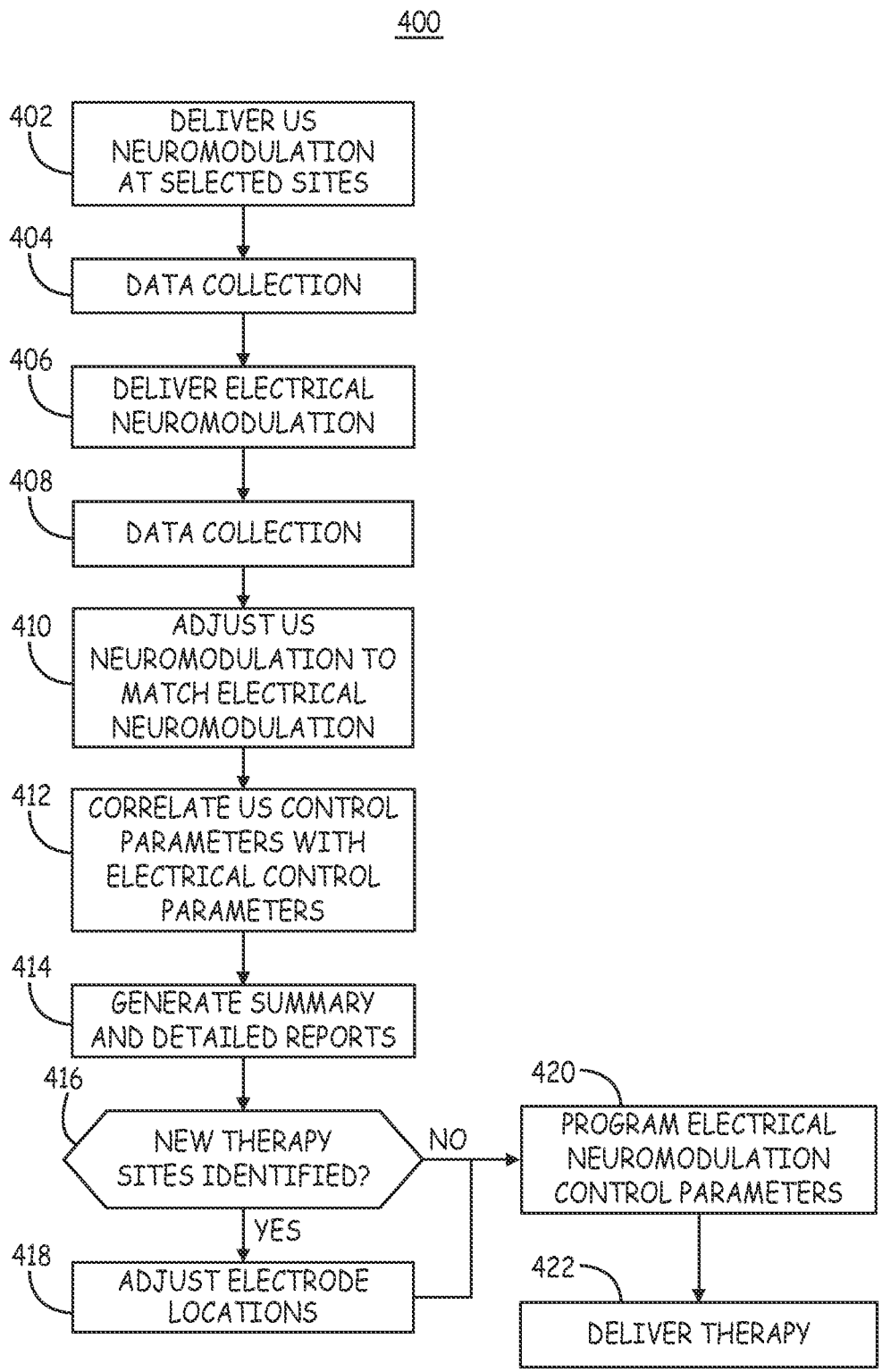
FIG. 8 is a flow chart of a method for operating the system shown in FIG. 7 for managing neuromodulation therapy in a patient.

With continued reference to FIG. 7, FIG. 8 is a flow chart 400 of a method for operating the system 600 shown in FIG. 7 for managing neuromodulation therapy in a patient. At block 402, ultrasound (US) neuromodulation is delivered at selected target sites. For example, ultrasound control unit 606 may control array 602 to focus ultrasound waveforms along therapy pathways 620 corresponding to potential new therapy target site(s) 634 or therapy pathways 622 corresponding to the existing electrical neuromodulation target site 632. Focusing of emitted ultrasound waveforms from array 602 may be controlled to target specific locations within target site 632 away from electrode 612 and 614 locations, at electrode 612 or 614 locations, along a pathway traversed by lead 610, and/or along alternative pathways that could be traversed by lead 610 or a new lead that may be introduced to target new therapy sites.

Because the ultrasonic stimulation can be used to activate or inhibit or block neural activity, ultrasound waveforms may be focused at dual or multi-site locations to simulate the effects of cathodes and anodes. Therefore, focusing of ultrasound energy at multiple sites (one or more sites to stimulate the tissue and one or more other sites to inhibit stimulation) can be used to determine effective electrode combinations and the types of leads that should be used for delivering or steering electrical stimulation with implanted electrodes.

Data is collected at block 404 to measure responses to the ultrasound modulation. The collected data may be ultrasound imaging data as described previously herein for identifying or confirming target sites and/or measuring a functional response at a therapy delivery site or a different monitoring site. The collected data may include electrical signals measured by electrodes 612 and 614. Other user-entered data, imaging data or other physiological signals may be acquired. Examples of various amplifier circuits and other systems that may be used to measure physiological signals and/or otherwise acquire imaging data are set forth above.

At block 406, electrical neuromodulation is delivered and the same type of data is collected at block 408 as at block 406 to enable comparative analyses of the effects of electrical neuromodulation and ultrasound neuromodulation. Such comparisons will enable a clinician to identify new therapy target sites and optimal therapy control parameters.

At block 410, the ultrasound waveform control parameters used to focus ultrasound energy at an electrode (612, 614) location may be adjusted to match a response to electrical stimulation at the electrode site. Further adjustment of the ultrasound waveform control parameters and the electrical stimulation control parameters will allow a correlation of ultrasonic neuromodulation control parameters to electrical neuromodulation control parameters to be made at block 412. The ultrasound waveform control parameters that produce the same or similar response as a particular set of electrical stimulation parameters can be identified.

This correlation can be performed in an automated manner in one example. For instance, logic may be provided to search the collected data for a same or similar response evoked between ultrasound waveform parameters and electrical stimulation parameters. When similar responses are located, the ultrasound waveform parameters may be automatically associated with the electrical waveform parameters. This may be accomplished, for instance, by storing some information along with the ultrasound waveform parameters that identifies the electrical waveform parameters that evoked a similar or same response (e.g., by storing pointers, identifiers, etc.). Alternatively, some information may be stored along with the electrical waveform parameters identifying the ultrasound waveform parameters that evoked a similar or same response, or the two types of parameters may be stored together. Those skilled in the art will appreciate that such associations may be created in many ways using various types of automated logic. Such logic may be provided by one or more data processing systems that may be communicatively coupled with, or alternatively separate from, one or more of control units 606 or 616 of FIG. 7. In some cases, the logic to perform the correlation may be provided, at least in part, by at least one of control unit 606 or 616. Logic of a type that may provide this type of automated correlation may comprise one or more software or firmware programs, one or more controllers, digital signal processors (DSPs), one or more other types of processors, application specific integrated circuits (ASICs), field-programmable gate array (FPGAs), or equivalent discrete or integrated logic circuitry, or other electronic circuitry or suitable components that provide the described functionality.

The volume of tissue activated by ultrasound neuromodulation may be determined via a functional imaging technique during data collection. A relationship may be determined between the volume of tissue activated via ultrasonic stimulation and the volume of tissue that must be activated via electrical stimulation to achieve the same effect. Examples of mechanisms for determining volumes of tissue activated via electrical stimulation and/or for configuring electrical stimulation parameters based on activated tissue are provided in commonly-assigned U.S. Pat. No. 7,822,483 entitled "Electrical and Activation Field Models for Configuring Stimulation Therapy", and provisionally-filed U.S. patent application Ser. No. 61/638,801 filed Apr. 26, 2012 entitled Visualizing Tissue Activated by Electrical Stimulation" and having Ser. No. 61/648,655 filed May 18, 2012 entitled "Techniques for Determining Volume of Tissue Activated", all of which are incorporated herein by reference to the extent to which these disclosures do not conflict with the current disclosure.

The volume of tissue activated by ultrasound at a target site for achieving therapeutic benefit may be correlated to electrical stimulation parameters required to activate the same volume of tissue. The data required to determine these correlations may be obtained through empirical studies. Once the required volume of tissue activated via electrical stimulation is determined, the electrode location and electrical parameters may be computed. These electrical stimulation control parameters can then be tested to verify a desired response.

At block 414, data analysis is performed to generate detailed and summary reports correlating ultrasonic neuromodulation parameters to electrical neuromodulation parameters as well as identifying an optimal therapy delivery plan. Results may be presented superimposed on a 2- or 3-dimensional image of the patient's anatomy. The optimal therapy delivery plan may include new therapy sites and corresponding therapy delivery control parameters and/or new control parameters for delivering therapy at existing electrical stimulation sites.

The optimal therapy delivery plan may give an indication of energy usage or battery longevity for the control unit 616 when embodied as an implantable unit. This enables a clinician to select a therapy delivery device having adequate prime cell battery capacity or rechargeable battery capacity for sustaining the intensity and duty cycle of the optimized therapy.

If new therapy sites are identified to effectively reduce or eliminate symptoms, as determined at block 416, electrode locations may be adjusted for delivering electrical neuromodulation. Adjustment of electrode locations at block 418 may include repositioning existing electrodes, removing existing electrodes, and/or positioning new electrodes. In some embodiments, a combination of electrical and ultrasonic neuromodulation therapy may be selected for the patient in which case an ultrasound transducer array may be positioned at block 418 for therapy delivery.

At block 420, the therapy control parameters are programmed according to the optimal therapy control parameters identified in the reports. The programmed therapy is delivered at block 422.

As may be appreciated, in some instances, the various steps of FIG. 8 may be rearranged, and in other cases, some steps may be omitted entirely, without departing from the scope of the disclosure. In any case, the steps of the method of FIG. 8 may be used to develop a knowledge base that correlates various electrical stimulation locations and parameters with ultrasound stimulation locations and parameters. Such a knowledge base may be developed, for instance, by delivering ultrasound neuromodulation and collecting data according to steps 402 and 404, respectively, on a population of patients that is already implanted with electrical stimulation electrodes. Once such a knowledge base is available, the collected data may be used to determine which patients may benefit from electrical stimulation. This type of knowledge base may also be used to select device types (e.g., lead types, neurostimulation device types, etc.), implant trajectories, electrode locations and programming parameters based on the ultrasound diagnostics for patients that are determined to be appropriate candidates for receiving electrical stimulation or chronic ultrasound stimulation. This type of analysis may greatly reduce the time required to plan an implant procedure, minimize potential side effects, optimize therapy benefits, and greatly reduce the burden to program a stimulation device with optimal therapy parameters. In addition, the availability of non-invasive ultrasound stimulation as described herein provides patients with an opportunity to experience the benefits and/or side effects associated with stimulation therapy prior to undergoing invasive surgery, thereby allowing a much more informed decision to be made concerning therapy options.

Using the techniques described herein, an automated process to systematically deliver ultrasonic stimulation to neural structures and/or circuits to diagnose a patient condition and/or measure a therapy response is provided. Acquired data is used to automatically identify therapy delivery sites and therapy delivery parameters that will lead to efficacious neuromodulation with minimal side effects. The therapy delivery modality, i.e. ultrasound, electrical, pharmaceutical or other, may then be selected and managed using the results of the ultrasound neuromodulation study. The systems and associated methods enable a large amount of detailed data to be acquired and analyzed in a time efficient manner, reducing clinician burden and potentially increasing the number of patients benefiting from neuromodulation therapy.

Thus, neuromodulation systems and associated methods have been presented in the foregoing description with reference to specific embodiments. It is appreciated that various modifications to the referenced embodiments may be made without departing from the scope of the disclosure as set forth in the following claims.

The invention claimed is:

1. A system comprising a neuromodulation therapy planning system and a neuromodulation therapy delivery system that is different than the neuromodulation therapy planning system, the neuromodulation therapy planning system comprising:

an ultrasound transducer array comprising at least one ultrasound transducer, the array adapted for external application to a portion of a patient's body; and a control unit comprising:

an ultrasound control unit coupled to the ultrasound transducer array and configured to control, at a first time, delivery of ultrasound waveforms for causing neuromodulation of neural tissue in a patient that simulates neuromodulation of the neural tissue that would be caused by electrical stimulation via an implantable electrical stimulation system of the neuromodulation therapy delivery system;

a data collection unit to acquire data indicating a response to the neuromodulation;

a data analysis unit configured to analyze the acquired data to accumulate correlation data between a response to the neuromodulation and an ultrasound control parameter used to deliver the ultrasound waveforms; and a reporting module configured to report the correlation data to enable identification of at least one therapy parameter; and the neuromodulation therapy delivery system comprising:
the implantable electrical stimulation system, wherein the implantable electrical stimulation system is configured to deliver, at a second time that is after the first time, electrical stimulation therapy as the neuromodulation therapy to the patient using the identified at least one therapy parameter.

2. The system of claim 1, wherein acquiring data comprises receiving reflections of ultrasound waveforms from the array.

3. The system of claim 2, wherein the control unit is further configured to control the array to emit first ultrasound waveforms for causing neuromodulation according to a first set of waveform control parameters and control the array to emit second ultrasound waveforms according to a second set of waveform control parameters, the second set of waveform control parameters different than the first of waveform control parameters.

4. The system of claim 3, wherein the control unit is further configured to identify a target site in response to the reflections, and control the array to focus the waveforms at the target site.

5. The system of claim 4, wherein controlling the array to focus the waveforms comprises at least one of adjusting a selection of transducers of the array enabled to emit ultrasound waveforms, adjusting a waveform phase, and adjusting an acoustic lens coupled to a transducer of the array.

6. The system of claim 2, wherein the control unit is configured to determine a functional response to the neuromodulation in response to the reflections.

7. The system of claim 1, wherein the neuromodulation therapy planning system further comprises:
a plurality of electrodes;
the control unit coupled to the plurality of electrodes and configured to control electrical stimulation delivery via the plurality of electrodes for causing neuromodulation of neural activity,
the control unit determining a correlation between a set of electrical stimulation control parameters and a set of ultrasound waveform control parameters in response to the data.

8. The system of claim 7, wherein the control unit is configured to adjust the set of electrical stimulation control parameters in response to the data.

9. The system of claim 7, wherein determining the correlation comprises determining a volume of tissue modulated by the ultrasound waveforms.

10. The system of claim 1, wherein:
the at least one therapy parameter includes a target site for delivering the neuromodulation therapy by the implantable electrical stimulation system,
the ultrasound control unit is configured to control delivery of the ultrasound waveforms by at least controlling the array to deliver ultrasound waveforms for causing neuromodulation of neural tissue in a patient at a plurality of neural sites,
the data collection unit is configured to acquire the data at least in part by acquiring data indicating a response to the neuromodulation for each of the plurality of neural sites, the data analysis unit is further configured to identify, based at least in part on the data indicating the response to the neuromodulation acquired for each of the plurality of neural sites, the target site for delivering the neuromodulation therapy by the implantable electrical stimulation system, and the implantable electrical stimulation system is configured to deliver the neuromodulation therapy at the identified target site.

11. The system of claim 1, wherein:
the at least one therapy parameter includes a trajectory for delivery of a therapy delivery device of the implantable electrical stimulation system,
the ultrasound control unit is configured to control delivery of the ultrasound waveforms by at least controlling the array to deliver ultrasound waveforms for causing neuromodulation of neural tissue in a patient at a plurality of neural sites,
the data collection unit is configured to acquire the data at least in part by acquiring data indicating a response to the neuromodulation for each of the plurality of neural sites, and
the data analysis unit is further configured to identify, based at least in part on the data indicating the response to the neuromodulation acquired for each of the plurality of neural sites, the trajectory for delivery of the therapy delivery device.

12. The system of claim 1, wherein:
the ultrasound control unit is configured to control delivery of the ultrasound waveforms by at least controlling the array to deliver ultrasound waveforms for causing neuromodulation of neural tissue in a patient at a plurality of neural sites;
the data collection unit is configured to acquire the data at least in part by acquiring data indicating a response to the neuromodulation for each of the plurality of neural sites,
the data analysis unit is further configured to identify, based at least in part on the data indicating the response to the neuromodulation acquired for each of the plurality of neural sites, the at least one therapy parameter to be used to deliver the electrical stimulation therapy by the implantable electrical stimulation system to the patient, and
the implantable electrical stimulation system is configured to deliver the electrical stimulation therapy using the at least one therapy parameter identified by the data analysis unit.

13. The system of claim 12, wherein:
the neuromodulation therapy planning system further comprises a storage device to store correlations between ultrasound neuromodulation and electrical neuromodulation, and
the control unit is further configured to identify the at least one therapy parameter based at least in part on the correlations.

14. The system of claim 1, wherein:
the neuromodulation therapy planning system further comprises a storage device storing historical data corresponding to a patient population, and
the control unit is further configured to identify the therapy parameter using the historical data.

15. The system of claim 1, wherein the control unit is further configured to identify the therapy parameter based at least in part on a correlation of a measured response to the neuromodulation and a predicted response.

16. The system of claim 1, wherein the implantable electrical stimulation system is configured to deliver deep brain stimulation using the identified therapy parameter.

17. The system of claim 16, wherein:
the implantable electrical stimulation system comprises a lead carrying at least one electrode for delivering the deep brain stimulation, and the at least one therapy parameter comprises one or both of an electrode site and a trajectory of the lead.

18. The system of claim 1, wherein the ultrasound control unit receives data from the data collection unit and is configured to adjust control of the transducer array in response to the data in a closed loop.

19. The system of claim 1, wherein the control unit is further configured to identify the at least one therapy parameter to be used to deliver the neuromodulation therapy by the implantable electrical stimulation system of the neuromodulation therapy delivery system.

20. A method for planning and delivering a neuromodulation therapy, the method comprising:
    delivering, at a first time and via an ultrasound transducer array of a neuromodulation therapy planning system, ultrasound waveforms for causing neuromodulation of neural tissue in a patient that simulates neuromodulation of the neural tissue that would be caused by electrical stimulation via an implantable electrical stimulation system, wherein the ultrasound transducer array is configured to externally apply the ultrasound waveforms to a portion of a body of the patient and comprises at least one ultrasound transducer;
    acquiring data indicating a response to the neuromodulation;
    analyzing the acquired data to determine correlation data between a response to the neuromodulation and an ultrasound control parameter used to deliver the ultrasound waveforms; and
    identifying, based on the correlation data, at least one therapy parameter to be used to deliver a neuromodulation therapy to the patient, wherein at least one of acquiring, analyzing, and reporting is performed by a control unit; and
    delivering, at a second time that is after the first time, to the patient and via a therapy delivery system that is different than the neuromodulation therapy planning system, the neuromodulation therapy using the identified therapy parameter.

21. The method of claim 20, wherein acquiring data comprises receiving reflections of ultrasound waveforms from the array.

22. The method of claim 21, further comprising delivering first ultrasound waveforms for causing neuromodulation according to a first set of waveform control parameters and delivering second ultrasound waveforms according to a second set of waveform control parameters, the second set of waveform control parameters different than the first set of waveform control parameters.

23. The method of claim 22, further comprising:
    identifying, via the control unit, a target site in response to the reflections; and
    controlling the array, via the control unit, to focus the waveforms at the target site.

24. The method of claim 23, wherein controlling the array to focus the waveforms comprises at least one of adjusting a selection of transducers of the array to emit ultrasound waveforms, adjusting a waveform phase, and adjusting an acoustic lens coupled to a transducer of the array.

25. The method of claim 21, further comprising determining a functional response to the neuromodulation in response to the reflections.

26. The method of claim 20, further comprising:
    delivering electrical stimulation via a plurality of electrodes of the neuromodulation therapy planning system for causing neuromodulation of neural activity; and
    determining a correlation between a set of electrical stimulation control parameters and a set of ultrasound waveform control parameters in response to the data.

27. The method of claim 26, further comprising adjusting the set of electrical stimulation control parameters in response to the data.

28. The method of claim 26, wherein determining the correlation comprises determining a volume of tissue modulated by the ultrasound waveforms.

29. The method of claim 20, wherein:
    the at least one therapy parameter includes a target site for delivering the neuromodulation therapy by the therapy delivery system
    delivering, via the ultrasound transducer array, the ultrasound waveforms comprises delivering, via the ultrasound transducer array, ultrasound waveforms for causing neuromodulation of neural tissue in a patient at a plurality of neural sites,
    acquiring the data comprises acquiring data indicating a response to the neuromodulation for each of the plurality of neural sites,
    the method further comprises:
        identifying, based at least in part on the data indicating the response to the neuromodulation acquired for each of the plurality of neural sites, the target site for delivering the neuromodulation therapy; and
        delivering, via the therapy delivery system, the neuromodulation therapy to the target site.

30. The method of claim 20, wherein:
    the at least one therapy parameter includes a trajectory for delivery of a therapy delivery device of the therapy delivery system,
    delivering, via the ultrasound transducer array, the ultrasound waveforms comprises delivering, via the ultrasound transducer array, ultrasound waveforms for causing neuromodulation of neural tissue in a patient at a plurality of neural sites,
    acquiring the data comprises acquiring data indicating a response to the neuromodulation for each of the plurality of neural sites, and
    the method further comprises:
        identifying, based at least in part on the data indicating the response to the neuromodulation acquired for each of the plurality of neural sites, the trajectory for delivery of the therapy delivery device; and
        delivering the therapy delivery device using the identified trajectory.

31. The method of claim 20, wherein the neuromodulation therapy comprises electrical stimulation therapy, the method further comprising:
    delivering, via the ultrasound transducer array, the ultrasound waveforms comprises delivering, via the ultrasound transducer array, ultrasound waveforms for causing neuromodulation of neural tissue in a patient at a plurality of neural sites;
    acquiring the data comprises acquiring data indicating a response to the neuromodulation for each of the plurality of neural sites;
    identifying, based at least in part on the data indicating the response to the neuromodulation acquired for each of the plurality of neural sites, at least one therapy parameter to be used to deliver the electrical stimulation therapy to the patient by the therapy delivery system; and
    delivering the electrical stimulation therapy using the identified at least one therapy parameter.

32. The method of claim 31, further comprising:
storing correlations between ultrasound neuromodulation and electrical neuromodulation in a storage device; and
identifying the at least one therapy parameter based on the stored correlations.

33. The method of claim 20, further comprising:
storing historical data corresponding to a patient population in the storage device; and
identifying the therapy parameter using the historical data.

34. The method of claim 20, further comprising identifying the therapy parameter in response to a correlation of a measured response to the neuromodulation and a predicted response.

35. The method of claim 20, wherein the therapy delivery system comprises an implantable electrical stimulation system, the neuromodulation therapy comprises electrical stimulation therapy, and wherein delivering the neuromodulation therapy comprises:
delivering, via the implantable electrical stimulation system, the electrical stimulation therapy using the identified therapy parameter.

36. The method of claim 35, wherein delivering the electrical stimulation therapy comprises delivering deep brain stimulation using the identified therapy parameter.

37. The method of claim 36, wherein the implantable electrical stimulation system comprises a lead carrying at least one electrode, and wherein the identified therapy parameter comprises one of an electrode site and a trajectory of the lead.

38. The method of claim 20, further comprising adjusting, via the control unit, the transducer array in response to the data received from the data collection unit in a closed loop manner.

39. The method of claim 20, wherein the therapy delivery system comprises an implantable therapy delivery system comprising at least one of an implantable electrode, an implantable ultrasound transducer, and an implantable drug delivery catheter.

40. A method comprising:
identifying, using a neuromodulation therapy planning system that includes an ultrasound transducer array externally positioned relative to a patient, one or more therapy parameters, wherein identifying the one or more therapy parameters comprises causing, at a first time, the ultrasound transducer array to deliver ultrasound waveforms for causing neuromodulation of neural tissue in the patient that simulates neuromodulation of the neural tissue that would be caused by electrical stimulation via an implantable electrical stimulation system; and
causing, at a second time that is after than the first time, the implantable electrical stimulation system implanted in the patient to deliver neuromodulation therapy to the patient using the identified one or more therapy parameters.

41. The method of claim 10, wherein identifying the one or more therapy parameters comprises:
identifying at least one of the one or more therapy parameters based on effects of the neuromodulation caused by the ultrasound waveforms.

42. The method of claim 40, wherein identifying the one or more therapy parameters further comprises:
causing the ultrasound transducer array to deliver ultrasound waveforms to cause neuromodulation of neural tissue in the patient at a plurality of neural sites; and
identifying a neural site of the plurality of neural sites based on effects of the neuromodulation at each of the neural sites,
wherein causing the implantable electrical stimulation system to deliver the neuromodulation therapy comprises causing the implantable electrical stimulation system to deliver the neuromodulation therapy at the identified site.

43. The method of claim 40, wherein the implantable electrical stimulation system comprises an implantable deep brain electrical stimulation system.

44. The method of claim 40, wherein identifying the one or more therapy parameters comprises identifying the one or more therapy parameters prior to the implantable electrical stimulation system being implanted into the patient.

* * * * *